(12) United States Patent
Andersen et al.

(10) Patent No.: US 6,291,447 B1
(45) Date of Patent: Sep. 18, 2001

(54) GRANULATIMIDE COMPOUNDS AND USES THEREOF

(75) Inventors: Raymond Andersen; Michel Roberge; Jasbinder Sanghera, all of Vancouver; Daniel Leung, Coquitlam; Edward Piers, Richmond, all of (CA); Roberto GS Berlinck, Sao Carlos, SP (BR); Robert Britton, Vancouver (CA)

(73) Assignees: The University of British Columbia; Kinetek Pharmaceuticals, Inc., both of Vancouver (CA)

( * ) Notice: Subject to any disclaimer, the term of this patent is extended or adjusted under 35 U.S.C. 154(b) by 0 days.

(21) Appl. No.: 09/258,991

(22) Filed: Feb. 26, 1999

(30) Foreign Application Priority Data

Mar. 13, 1998 (CA) .................................................. 2232074
Aug. 14, 1998 (CA) .................................................. 2245029

(51) Int. Cl.$^7$ ...................... C07D 487/14; C07D 487/22; A61K 31/415; A61K 31/44
(52) U.S. Cl. .......................... 514/183; 514/283; 514/393; 514/394; 540/469; 546/48; 546/52; 548/301.7
(58) Field of Search .................... 546/48, 52; 548/301.7; 540/469; 514/183, 283, 393, 394

(56) References Cited

U.S. PATENT DOCUMENTS

| | | | |
|---|---|---|---|
| 5,438,050 | 8/1995 | Kleinschroth | 514/183 |
| 5,489,608 | 2/1996 | Kleinschroth | 514/410 |
| 5,604,219 | 2/1997 | Murakata | 514/211 |
| 5,807,882 | 9/1998 | Coudert et al. | 514/410 |

FOREIGN PATENT DOCUMENTS

| | | |
|---|---|---|
| 35 35 842 A1 | 4/1987 | (DE) . |
| 0 328 000A2 | 2/1989 | (EP) . |
| 0 434 057 A2 | 6/1991 | (EP) . |
| 0 657 458 A1 | 6/1995 | (EP) . |
| 0 672 668 A1 | 9/1995 | (EP) . |
| 0 735 038 A1 | 10/1996 | (EP) . |
| 0 841 337 A1 | 5/1998 | (EP) . |
| WO 91/09034 | 6/1991 | (WO) . |
| WO 94/04541 | 3/1994 | (WO) . |
| WO 94/07895 | 4/1994 | (WO) . |
| WO 95/32974 | 12/1995 | (WO) . |
| WO 95/32975 | 12/1995 | (WO) . |
| WO 95/32976 | 12/1995 | (WO) . |
| WO 96/11933 | 4/1996 | (WO) . |
| WO 97/18809 | 5/1997 | (WO) . |
| WO 97/19080 | 5/1997 | (WO) . |

OTHER PUBLICATIONS

Roberge et al., High–Throughput Assay for G2 Checkpoint Inhibitors, Cancer Research, 58(24), pp. 5701–5706, Dec. 1998.*

Berlinck et al., Granulatimide and Isogranulatimide, J. Org. Chem. vol. 63, No. 26, pp. 9850–9856, Dec. 1998.*

Harris et al., Oxidative Cyclasations with Palladium Acetate, Tetrahedron Letters, vol. 34, No. 51, pp. 8361–8364, 1993.*

Terpin, et al Synthesis and Cyclisation of Didemnimide C and its Imidazol–1–yl Isomer[1] (1997) Tetrahedron vol. 54:1740–1752.

(List continued on next page.)

Primary Examiner—Mukund J. Shah
Assistant Examiner—Deepak R. Rao
(74) Attorney, Agent, or Firm—Pamela J. Sherwood; David Parker

(57) ABSTRACT

Novel granulatimide compounds and pharmaceutical formulations thereof are provided. Compounds of this invention have the general formula:

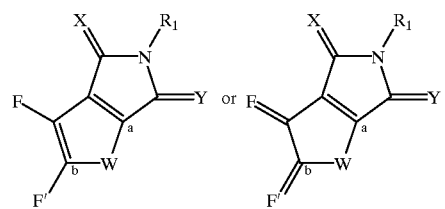

wherein are independently R or Z as defined below, or in combination F and F' is $Ar_1$ as defined below;

$Ar_1$ is a monocyclic, bicyclic or tricyclic, fully or partially aromatic system containing five or six membered carbocyclic or, oxygen, nitrogen or sulphur containing heterocyclic rings, optionally substituted with R or Z;

W is selected from the group consisting of formula (i); (ii) or (iii), wherein the structures are as follows:

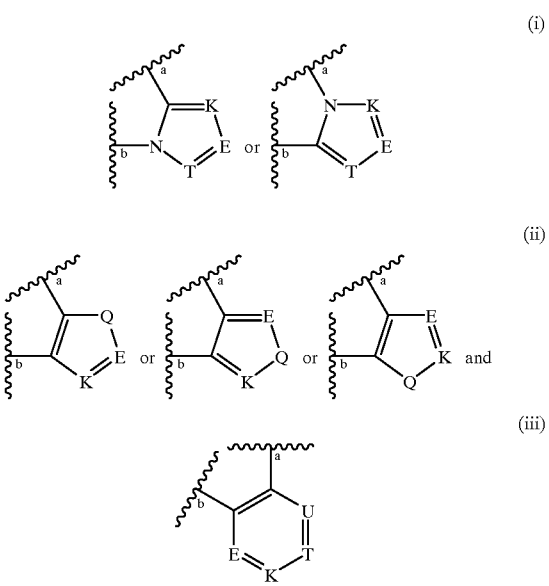

22 Claims, 2 Drawing Sheets

OTHER PUBLICATIONS

Russell, et al "Abrogation of the $G_2$ Checkpoint Results in Differential Radiosensitization of $G_1$ Checkpoint–deficient and $G_1$ Checkpoint–competent Cells[1]", (1995) Cancer Res. vol. 55:1639–1642.

Powell, et al "Differential Sensitivity of p53$^{(-)}$ and p53$^{(+)}$ Cells to Caffeine–induced Radiosensitization and Override of $G_2$ Delay[1]"., (1995) Cancer Res. vol. 55:1643–1648.

Wang, et al. "UCN–01:a Potent Abrogator of $G_2$ Checkpoint Function in Cancer Cells With Disrupted p53", (1996) J. Nat'l. Cancer Inst. vol. 88:956–965.

Downes, et al. "Caffeine Overcomes a Restriction Point Associated with DNA Replication, but Does Not Accelerate Mitosis", (1990) J. Cell Biol. vol. 110:1855–1859.

Bracey, et al. "Inhibition of Radiation–induced $G_2$ Delay Potentiates Cell Death by Apaptosis and/or the Induction of Giant Cells in Colorectal Tumor Cells with Disrupted p53 Function[1]", (1997) Clin. Cancer Res. vol 3:1371–1381.

Steinman, et al. "Chemically induced premature mitosis: Differential response in rodent and human cells and the relationship to cyclin B synthesis and p34$^{cdc2}$/cyclin B complex formation", (1991) P.N.A.S. vol. 88:6843–6847.

Schlegel "Caffeine–Induced Uncoupling of Mitosis form the Completion of DNA Replication in Mammalian Cells" (1986) Science vol. 232:1264–1266.

Yao et al "Selective radiosensitization of p53–deficient cells by caffeine–mediated activation of p34$^{cdc2}$ kinase"., (1996) Nature Med.vol.2:1140–1143.

Russell, et al. "Preferential Radiosensitization of G1 Checkpoint–Deficient Cells by Methylxanthines", (1996) Int. J.Radiat. Oncol. Biol. Phys. vol.36:1099–1106.

Tam, et al. "Staurosporine Overrides Checkpoints for Mitotic Onset in BHK Cells[1]" (1992) Cell Growth Differ. vol.3:811–817.

Andreasson, et al. "2–Aminopurine overrides multiple cell cycle checkpoints in BHK cells", (1992) P.N.A.S. vol.89:2272–2276.

Busse, et al. "The Action of Caffeine on X–Irradiated HeLa Cells" (1978) Radiat. Res. vol. 76:292–307.

Vervoot et al. "Didemnimides A–D: Novel, Predator–Deterrent Alkaloids from the Caribbean Mangrove Ascidian *Didemnum conchyliatum*", (1997) J. Org.Chem. vol 62:1486–1490.

Smith, et al. "The Chemistry of 3–( –Cyanobenzylidene)–1–phenyltriazenes and Their Conversion to Diarylmaleimides and Phenanthrene–9, 10–dicarboximides", (1990) J. Organic Chemistry, vol. 55, No. 10, pp 3351–3361.

* cited by examiner

GRANULATIMIDE COMPOUNDS AND USES THEREOF

BACKGROUND

Natural products are a rich source of novel organic compounds, many of which have interesting and desirable biological activities. From extracts of an organism of interest, such as marine invertebrates, methods of chemical separation and analysis may be applied to elucidate the structure of biologically active compounds. These chemical structures then form the basis for synthetic modifications to enhance the desired activity.

Marine ascidians, or sea squirts, have a number of unique secondary metabolites with potent biological activity. Colonial ascidians within the family Didemnidae have been particularly prolific, containing nitrogenous amino acid derived metabolites, including various cyclic peptides. The compounds termed didemnimides were isolated from *Didemnum conchyliatum*. These compounds are indole-maleimide-imidazole alkaloids, which could hypothetically be synthesized as a condensation of tryptophan and histidine The further study of Didemna products, and the characterization of their active agents, is of particular interest for the development of novel therapeutic agents and uses thereof.

Relevant Literature

Didemnimide compounds are described by Vervoot et al. (1997) *J. Org. Chem.* 62:1486–1490. In describing synthesis of such didemnimide compounds, Terpin et al. (1998) *Tetrahedron* 54:1740–1752 reported a ring closing event that may occur upon irradiation or upon recrystallization from methanol of a Boc protected intermediate used in the didemnimide synthesis scheme.

Known G2 checkpoint inhibitors include purine analogues, e.g. caffeine, pentoxifylline, 2-aminopurine, 6-dimethylaminopurine; and staurosporine with its derivative UCN-01 (7-hydroxystaurosporine). See, for example, Busse et al. (1978) *Radiat. Res.* 76:292–307; Schlegel (1986) *Science* 232:1264–1266; Downes et al (1990) *J. Cell. Biol.* 110:1855–1859; Steinmann et al. (1991) *P.N.A.S.* 88:6843–6847; Andreasson et al. (1992) *P.N.A.S.* 89:2272–2276; Tam et al. (1992) *Cell Growth Differ.* 3:811–817; and Wang et al. 1996) *J. Nat'l Cancer Inst.* 88:956–965.

Experiments employing cells deficient in the tumour suppressor protein p53 have demonstrated the value of the two groups of G2 checkpoint inhibitors described above, for selectively sensitizing cancer cells. Pentoxifylline has been shown to enhance cisplatin induced killing of p53-MCF-7 cells 30-fold and radiation induced killing of p53-A549 human lung adenocarcinoma cells 5-fold. For example, see Russell et al. (1995) *Cancer Res.* 55:1639–1642; Powell et al. (1995) *Cancer Res.* 55:1643–1648; Russell et al. (1996) *Int. J. Radiat. Oncol. Biol. Phys.* 36:1099–1106; Yao et al. (1996) *Nature Med.* 2:1140–1143; and Bracey et al (1997) *Clin. Cancer Res.* 3:1371–1381.

SUMMARY OF THE INVENTION

Granulatimide compounds of Formula I are provided, as defined herein. This invention includes the naturally occurring compounds, granulatimide and iso-granulatimide, in purified or partially purified form, including extracts containing these compounds taken from naturally occurring sources, e.g. *Didemnum granulatum*. In one embodiment of the invention, formulations of the compounds in combination with a physiologically acceptable carrier are provided.

The pharmaceutical formulations are useful as a cytotoxic agent; as a protein kinase inhibitor; and to inhibit the G2 checkpoint. This invention also provides the use of compounds of Formula I, e.g. to sensitize cells to the effects of DNA damaging agents; and the use of such compounds in the formulation of agents, including medicaments.

BRIEF DESCRIPTION OF THE DRAWINGS

FIG. 1(A) G2 checkpoint inhibition by iso-granulatimide; FIG. 1(B) iso-granulatimidend γ-irradiation kill p53$^-$ cells synergistically (MCF-7 mp53 cells seeded at 1000 cells per well in 96-well plates were grown overnight and irradiated with 0 Gy (O), 2 Gy (■), 4 (●) or 6 Gy (♦), immediately after irradiation the cells were treated with iso-granulatimide for 16 h, cell survival was measured using a soluble tetrazolium salt assay (CellTiter96™Promega), 100% cell survival is defined as the surviving fraction after irradiation alone (6 Gy induced about 80% cell death); and FIG. 1(C) iso-granulatimidend γ-irradiation do not kill p53+ cells synergistically (method identical to (B) except that MCF-7 cells are used).

DETAILED DESCRIPTION OF EMBODIMENTS OF THE INVENTION

Figure 1:
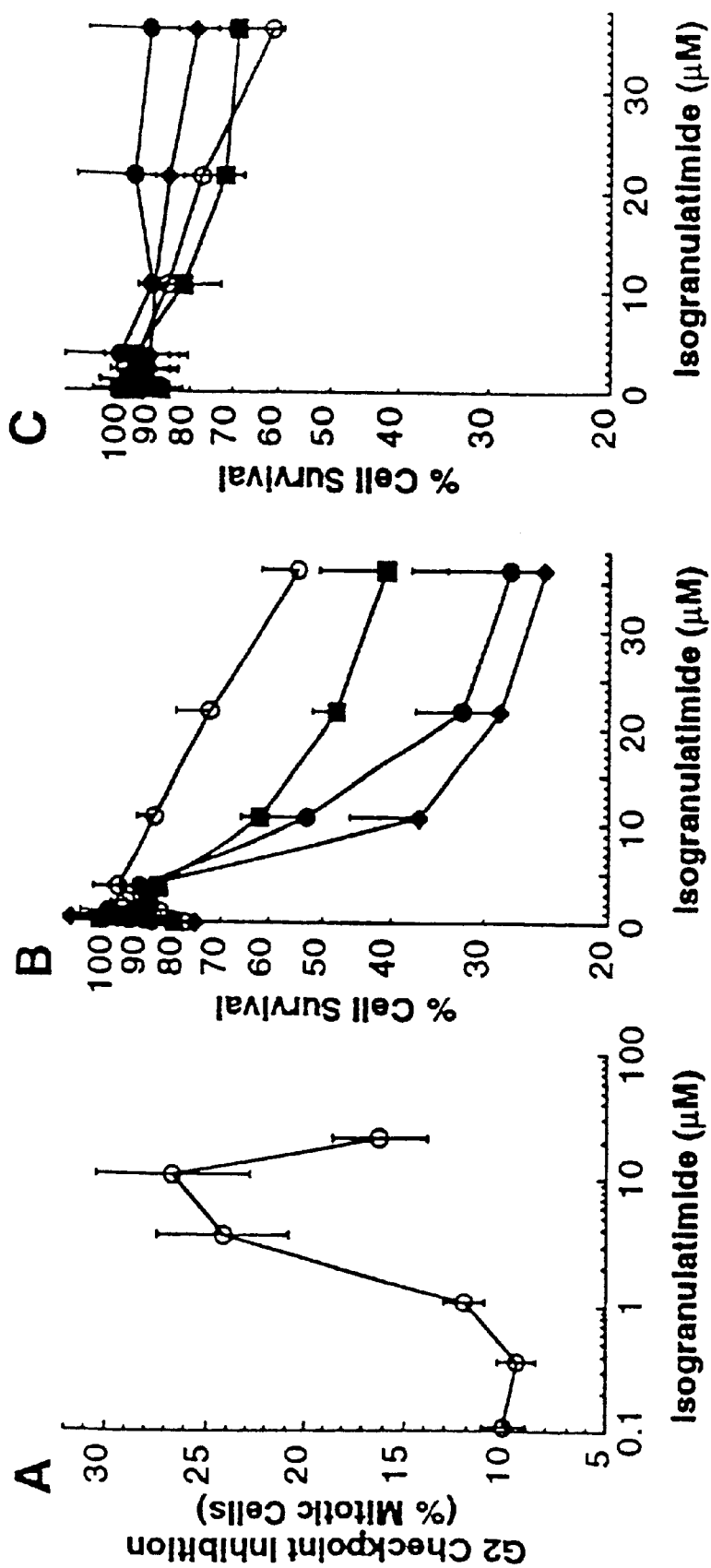
FIGS. 1A to 1C are a series of graphs showing.

Novel granulatimide compounds of Formula I are provided. This invention includes the naturally occurring compounds, granulatimide and iso-granulatimide, in purified or partially purified form, including extracts containing these compounds taken from naturally occurring sources. In one embodiment of the invention, formulations of the compounds in combination with a physiologically acceptable carrier are provided.

The pharmaceutical formulations are useful as a cytotoxic agent; and to inhibit protein kinases, including those that act to regulate the G2 checkpoint. Such G2 checkpoint inhibition prevents arrest, or releases cells that are arrested at this checkpoint, thereby permitting the cells to proceed to mitosis. This invention also provides the use of compounds of Formula I to sensitize cells to the effects of DNA damaging agents; and the use of such compounds in the formulation of agents, including medicaments, for potentiating the effect of DNA damaging agents on cells.

DEFINITIONS

It is to be under stood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a compound" includes a plurality of such compounds and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Granulatimide compounds: as used herein, the term "granulatimide compound" is used generically to describe a class of compounds having the structure as follows in Formula I. Included in this genus are the naturally occurring compounds granulatimide and iso-granulatimide. Compounds of this invention designated herein as being compounds of Formula I have the following structure, including all stereoisomers thereof when the compound may exist as stereoisomers:

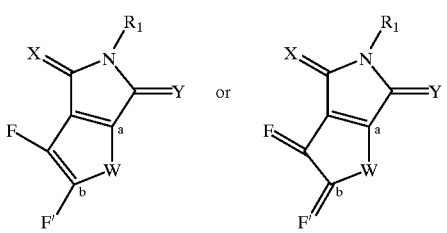

Formula I wherein:
F and F' are independently R or Z as defined below, or in combination F and F' is $Ar_1$ as defined below;
$Ar_1$ is a monocyclic, bicyclic or tricyclic, fully or partially aromatic system containing five or six membered carbocyclic or, oxygen, nitrogen or sulphur containing heterocyclic rings, optionally substituted with R or Z;
W is selected from the group consisting of formula (i); (ii) or (iii), wherein the structures are as follows:

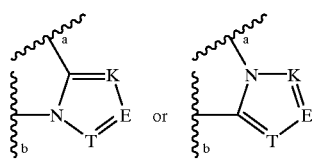

(i)

in which K, E and T are independently selected from the group consisting of: N, CR, and CZ, and wherein R and Z are as defined below;

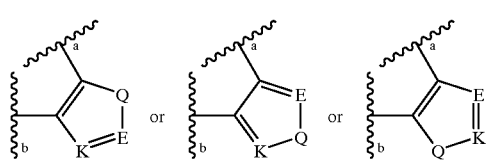

(ii)

in which K and E are independently selected from the group consisting of: N, CR and CZ, and wherein R, Z and Q are as defined below; and

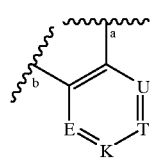

(iii)

in which K, E, T and U are independently selected from the group consisting of: N, CR and CZ, and wherein R and Z are as defined below;
$R_1$, is selected from the group consisting of: R; RCO—; $Ar_2CO$—; and, $Ar_2CH_2$—, wherein $Ar_2$ is an aromatic substituent selected from the group consisting of: phenyl, naphthyl, anthracyl, phenanthryl, furan, pyrrole, thiophene, benzofuran, benzothiophene, quinoline, isoquinoline, imidazole, thiazole, oxazole, and pyridine, and $Ar_2$ may be optionally substituted with R or Z, wherein R and Z are as defined below;
R is selected from the group consisting of: H; and a structural fragment having a saturated or unsaturated linear, branched, or cyclic, skeleton containing one to ten carbon atoms in which the carbon atoms may be optionally substituted with a substituent selected from the group consisting of: —OH; —$OR_3$; —$O_2CR_3$; —SH; —$SR_3$; —$SOCR_3$; —$NH_2$; —$NHR_3$; —$NH(R_3)_2$; —$NHCOR_3$; $NRCOR_3$;—I; —Br; —Cl; —F; —CN; —$CO_2H$; —$CO_2R_3$; —CHO; —$COR_3$; —$CONH_2$; —$CONHR_3$; —$CON(R_3)_2$; —COSH; —$COSR_3$; —$NO_2$; —$SO_3H$; —$SOR_3$; and —$SO_2R_3$, wherein $R_3$ is a linear, branched or cyclic, one to ten carbon saturated or unsaturated alkyl group;
Z is an optional substituent selected from the group consisting of: H; —OH; —OR; —$O_2CR$; —SH; —SR; —SOCR; —$NH_2$; —NHR; —$NH(R)_2$; —NHCOR; NRCOR; —I; —Br; —Cl; —F; —CN——$CO_2H$; —$CO_2R$; —CHO; —COR; —$CONH_2$; —CONHR; —$CON(R)_2$; —COSH; —COSR; —$NO_2$; —$SO_3H$; —SOR; and, —$SO_2R$;
Q is selected from the group consisting of: $NR_1$; O; S, and $C(R)_2$; and
X and Y are independently selected from the group consisting of: O; H, OH; and $H_2$.

In a preferred embodiment of the invention, F and F' are a bicyclic aromatic system comprising a five-membered and a six-membered ring, having the structure as follows:

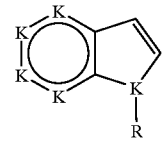

wherein each K is independently selected from the group consisting of N, CR and CZ, wherein Z is as previously defined. R is as previously defined, wherein R is selected from the group consisting of H; and a structural fragment having a saturated or unsaturated linear, branched, or cyclic, skeleton containing one to ten carbon atoms in which the carbon atoms may be optionally substituted with a substituent selected from the group consisting of: —OH; —$OR_3$; —$O_2CR_3$, —SH; —$SR_3$; —$SOCR_3$; —$NH_2$; —$NHR_3$; —$NH(R_3)_2$; —$NHCOR_3$; $NRCOR_3$; —I; —Br; —Cl; —F; —CN; —$CO_2H$; —$CO_2R_3$; —CHO; —$COR_3$; -$CONH_2$; -$CONHR_3$; —$CON(R_3)_2$; —COSH; —$COSR_3$; —$NO_2$; —$SO_3H$; $SOH_3H$; —$SOR_3$; and —$SO_2R_3$, wherein $R_3$ is a linear, branched or cyclic, one to ten carbon saturated or unsaturated alkyl group. Of particular interest is the F/F' group having the structure:

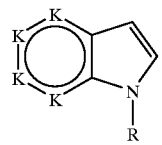

Where the granulatimide compound comprises the above F/F' group, the W group of formula (ii) may be used, to provide the structure shown in Formula II.

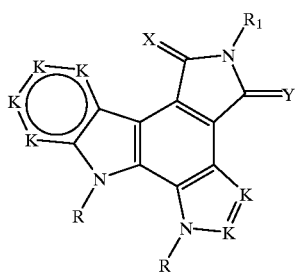

The compound of Formula II may be further derivatized by the addition of various functional groups, as shown in Formula III Formula III

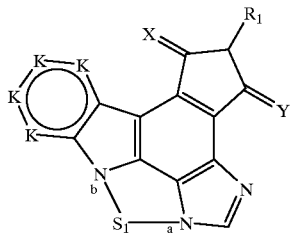

Where S1 is selected from the group consisting of

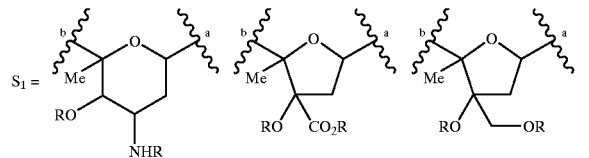

wherein K, X, Y and $R_1$ are as defined above, and R is an alkyl group of from 1 to 6 carbon atoms, branched or unbranched, linear or circular.

Alternatively, the granulatimide compound is derivatized as set forth in Formula IV:

Formula IV

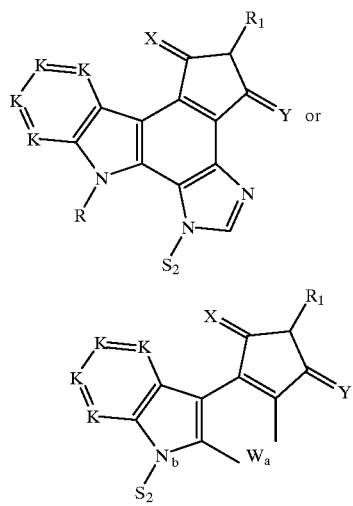

where K, X, Y and $R_1$ are as defined above, R is H or an alkyl of from one to six carbon atoms; and S2 has the formula (iv)

(iv)

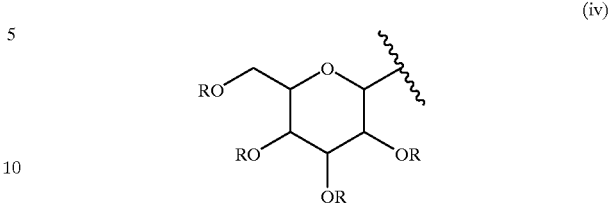

or $S_2$ is a linear alkyl chain of from one to eight carbon atoms containing a terminal $NR_2$, where $R_2$ is an alkyl group of from 1 to 6 carbon atoms, branched or unbranched, linear or circular.

In another alternative embodiment, the granulatimide compound has the structure shown in Formula V:

Formula V

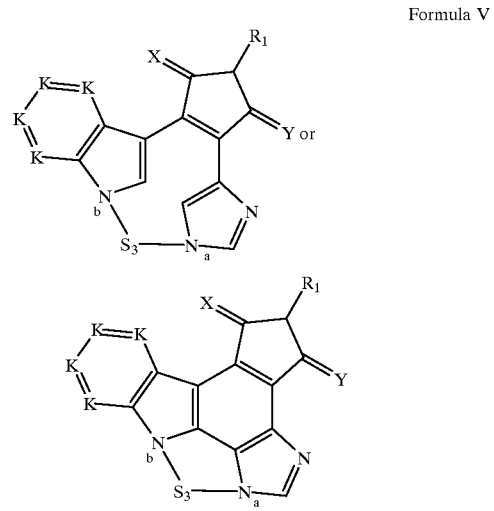

where K, X, Y and $R_1$ are as defined above, and $S_3$ is

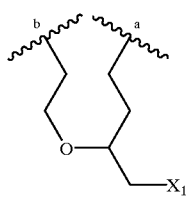

and $X_1$ is selected from the group of $N(CH_3)_2$, $NHCH_3$, $NH_2$,

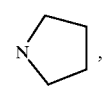

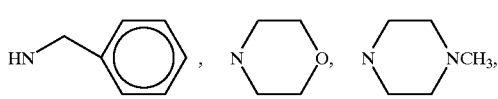

or $S_3$ is a linear bridge of between five and eight carbon, nitrogen or oxygen atoms, where the bridge carbon atoms may have OR or NR$_2$ substituents and the bridge nitrogen atoms may have R substituents, where R is as defined above.

Preferred structures for W are the five membered rings described above, more preferably comprising one or two nitrogen atoms. Preferably, E, K, T and U (where present) are: N or CH. Also, preferably Q is NH. Also preferably, R$_1$ is: H or CH$_3$. Also preferably, X and Y are oxygen. The following are examples of compounds of Formula 1 in which F and F' are Ar$_1$, with each of K, Q, R and Z being independently as defined above.

i)
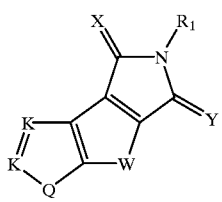

ii)
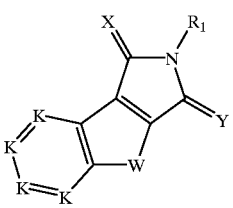

iii)
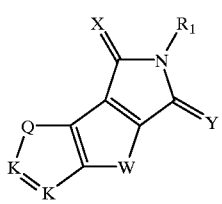

iv)
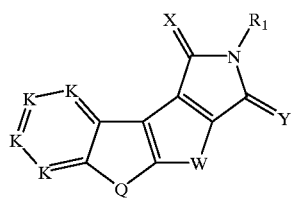

v)
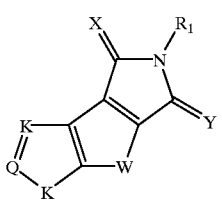

vi)
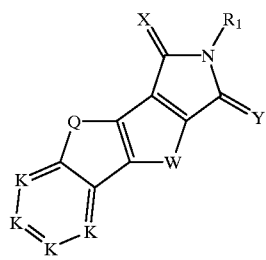

-continued vii)
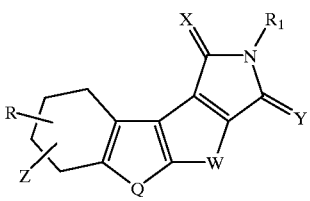

viii)
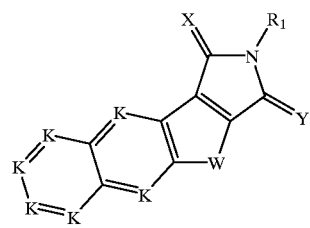

In one embodiment of the invention, the granulatimide compound comprises a basic nitrogen at either position 16 or 17, according to the number scheme shown below on Formula II (as previously described).

Formula II
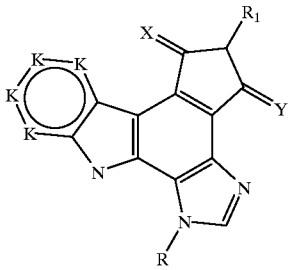

Preferably, excluded as granulatimide compounds of the invention are derivatives comprising a protecting group, e.g. Boc, etc., at the position corresponding to 1 in the above scheme.

Preferred compounds of Formula I are as follows, with substituents as defined above or as particularly defined below, where "Me" represents a methyl substituent throughout.

1
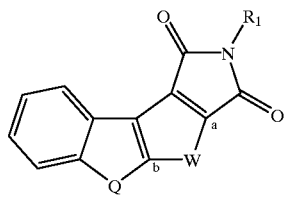

wherein Q=NH; R₁=H; and each of K, E, T=N or CH;

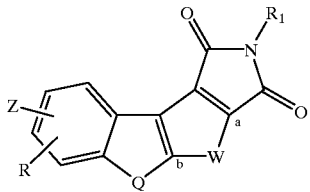

wherein Q=NH; R₁=H; and each of K, E, T=N or CH;

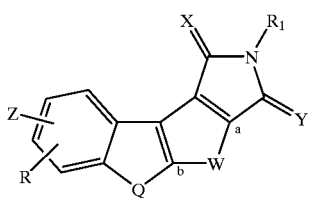

wherein Q=NH or NMe; R₁=H or Me; and each of K, E, T=N or CH;

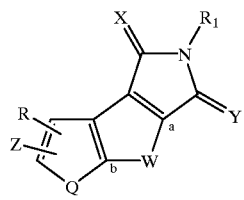

wherein Q=NH or NMe; R₁=H or Me; and each of K, E, T=N or CH;

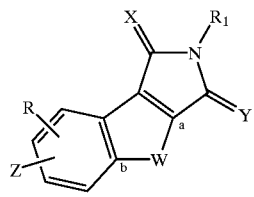

wherein Q=NH or NMe; R₁=H or Me; and each of K, E, T=N or CH; and

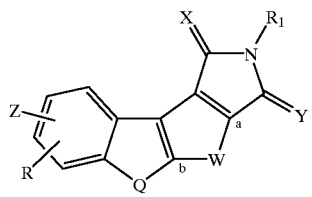

wherein Q=NH or NMe; R₁=H or Me; and each of K, E, T=N or CH.

In one embodiment of the invention, the granulatimide compound is one of the naturally occurring compounds: granulatimide, or iso-granulatimide.

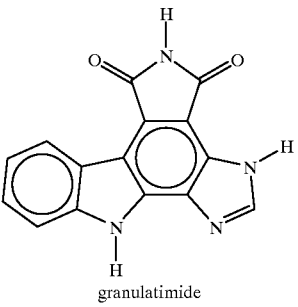

granulatimide

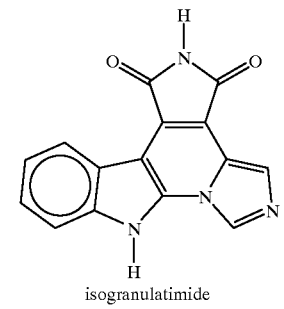

isogranulatimide

Pharmaceutically acceptable salts of the granulatimide compounds also fall within the scope of the compounds as disclosed herein. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable organic amine addition salts are salts with morpholine and piperidine. Examples of pharmaceutically acceptable amino acid addition salts are salts with lysine, glycine, and phenylalanine.

Protein Kinases and Inhibitors: These enzymes use the gamma phosphate of ATP or GTP to generate phosphate monoesters utilizing protein alcohol groups on serine or threonine, and/or protein phenolic groups (tyrosine) as phosphate group acceptors. They are related by virtue of their homologous kinase domains, which consist of 200–300 amino acid residues. The kinase domains impart the catalytic activity by binding and orientation of the phosphate donor as a complex with divalent cation; binding and orientation of the polypeptide substrate; and transfer of the γ-phosphate from the ATP or GTP to the acceptor hydroxyl residue. Protein kinases are involved in signaling pathways for such important cellular activities as responses to extracellular signals and cell cycle checkpoints. Inhibition of specific protein kinases provides a means of intervening in these signaling pathways, for example to block the effect of an extracellular signal, to release a cell from cell cycle checkpoint, etc.

Defects in the activity of protein kinases are associated with a variety of pathological or clinical conditions, where there is a defect in signaling mediated by protein kinases. Such conditions include those associated with defects in cell cycle regulation or in response to extracellular signals, e.g. hyperglycemia and diabetes type I and type II, immunological disorders, e.g. autoimmune and immunodeficiency diseases; hyperproliferative disorders, which may include psoriasis, arthritis, inflammation, cancer, etc.

Protein kinases of interest include those involved in cell cycle regulation, particularly at the G2 checkpoint. Other kinases of interest include those involved in the GSK3 and ILK signaling pathways. Glycogen synthase kinase-3 (GSK3) is implicated in the regulation of several physiological processes, including the control of glycogen and protein synthesis by insulin, modulation of the transcription factors AP-1 and CREB, the specification of cell fate and dorsoventral patterning. GSK3 is inhibited by serine phosphorylation in response to insulin or growth factors and in vitro by either MAP kinase-activated protein (MAPKAP) kinase-1 or p70 ribosomal S6 kinase.

Integrin-linked kinase (ILK) is an ankyrin-repeat containing serine-threonine protein kinase capable of interacting with the cytoplasmic domains of integrin beta1, beta2, and beta3 subunits. Overexpression of ILK in epithelial cells disrupts cell-extracellular matrix as well as cell-cell interactions, suppresses suspension-induced apoptosis, and stimulates anchorage-independent cell cycle progression. In addition, ILK induces nuclear translocation of beta-catenin, where the latter associates with a T cell factor/lymphocyte enhancer-binding factor 1 (TCF/LEF-1) to form an activated transcription factor.

The granulatimide compounds of the present invention act as specific protein kinase inhibitors, and are useful as therapeutic agents in treating conditions characterized by defects in signaling associated with these proteins.

G2 checkpoint Normal cells respond to DNA damage in one of two ways, depending upon their type and the degree of damage. The cells may activate an apoptotic pathway leading to suicide of the cell and its removal or, survival of a damaged cell may be promoted by activating checkpoints that temporarily halt the normal cycle of growth and division to allow time for DNA repair. The checkpoints operate during the G1 phase of the cycle so that DNA is repaired before it is replicated in the S phase; and, during the G2 phase so that DNA is repaired before chromosomes are segregated in the mitosis phase (M).

The subject granulatimide compounds are active in the inhibition of the G2 checkpoint. They are of interest as therapeutic reagents to treat hyperproliferative disorders, which may include psoriasis, arthritis, inflammation, cancer, etc. Administration of the subject compounds will release cells from the G2 checkpoint; and can result in apoptosis of the treated cells. Preferably the treated cells are unable to activate the G1 checkpoint. Many human tumors have mutations in the protein p53. As a result, they are unable to activate the GI checkpoint, but can still utilize the G2 checkpoint Inhibiting the checkpoint would drive tumor cells into mitosis, thereby increasing the effectiveness of cytotoxic agents that act by damaging DNA, e.g. cisplatin, bleomycin, and etoposide; and radiotherapy.

Over 50% of human cancers exhibit a loss of function of the protein p53. Cells with mutated p53 are unable to activate the G1 checkpoint in response to DNA damage. However, the G2 checkpoint (although usually weaker than in normal cells) still provides an opportunity to repair the DNA damage before cell division. Inhibition of the G2 checkpoint alone generally does not have a strong effect on normal cells, or tumor cells that retain normal G1 checkpoint activity. G2 checkpoint inhibitors used in combination with a DNA damaging agent will significantly increase the killing of cells that cannot activate the G1 checkpoint.

Throughout this specification, the term "G2" or G2 phase" means the phase of the cell cycle between the end of DNA synthesis and the beginning of mitosis A cell in G2 has an interphase nucleus as determined by microscopy, and duplicated DNA (usually determined by flow cytometry).

G2 checkpoint. Inhibitor Throughout this specification, the term "G2 checkpoint inhibitor" means a substance which is capable of releasing a cell from arrest in G2 phase brought about by DNA damage, preventing a cell from arrest in G2 phase in response to DNA damage, or both.

This invention provides a method of increasing the killing by DNA damage of cells having G1 checkpoint deficiency, comprising the steps of administering a DNA damaging agent to said cells thereby damaging DNA of said cells, and administering a G2 checkpoint inhibitor compound to said cells, wherein the G2 inhibitor compound is a compound of Formula I, or a pharmaceutically acceptable salt thereof.

Throughout this specification, the term "DNA damaging agent" means any substance or treatment which induces DNA damage in a cell, including UV irradiation, gamma irradiation, X-rays, alkylating agents, antibiotics that induce DNA damage by binding to DNA, inhibitors of topoisomerases and any compound used in chemotherapy which acts by causing DNA damage. Examples of specific compounds are cisplatin, VM-26, and procarbazine.

G2 Checkpoint Inhibitor Assay. The G2 checkpoint inhibitor assay described herein involves treating cells, e.g. cells associated with a hyperproliferative disorder, including cancer cells, with a DNA damaging agent under conditions whereby arrest of the cells at G2 will be induced. A sample to be tested for G2 checkpoint inhibition activity and an agent which arrests cells in mitosis are applied to the cells, following which it is determined whether the G2 checkpoint is overcome and the cells enter mitosis. Release of the cells from arrest at G2 or prevention of arrest at G2, such that the cells proceed to mitosis, is the indicator of G2 checkpoint inhibition activity.

The assay requires use of a cell culture in which the cells are incapable of arrest at the G1 checkpoint in response to DNA damage. The cells may be from any of the numerous cell lines for which it is known that the cells are incapable of arrest at G1. Such cells include cells which are p53 deficient, including: any cell line with a natural mutation or deletion in the p53 gene which renders p53 inactive; any cell line expressing a viral oncogene which disrupts p53; any cell line expressing dominant-negative mutant p53 (some mutant p53 proteins inhibit wild-type protein such as in the p53-MCF-7 cells used in the examples herein); and any primary or established cell line derived from p53 "negative transgenic" animals. Specific examples of suitable cells are the following: cells which have incorporated the human papillomavirus type-16 E6 gene, cell lines which are mutant for p53 function including Burkitt's human lymphoma cell line CA46 and the human colon carcinoma cell line HT-29 (CA46 and HT-29 are available from the American Type Culture Collection). Cell lines with a genetic deficiency which disrupts the G1 checkpoint other than by disruption of p53 may also be employed in this assay.

Once a cell line incapable of G1 arrest is chosen, conditions for arresting a majority of the cells at G2 in response to a DNA damaging agent are optimized by determining appropriate culture conditions, incubation time, and type and dosage of DNA damaging agent. Preferably, at least 50% of the cells in a culture will be arrested at G2 in response to the DNA damaging agent. Maximizing the proportion of cells in the population which are arrested at G2 will reduce the background signal.

Once the conditions for G2 arrest in the cell culture are established, the assay may be carried out in one of two ways. First, the cells may be arrested at G2 in response to the DNA damaging agent and then treated with the sample to determine whether there is release from G2 arrest or, the cells may be treated with the sample prior to the time when the majority of the cells would be expected to be arrested at G2 and determine whether the cells are prevented from G2 arrest.

Release from G2 arrest or prevention of G2 arrest is detected by a quantitative determination of the cells which proceed to mitosis. The assay culture is treated with a agent which will arrest such cells in mitosis. Such agents include microtubule depolymerizing agents that arrest cells in metaphase, such as nocodazole. This will prevent cells from exiting mitosis and entering the next cell cycle.

In the assay, determination of the cells which proceed to mitosis is carried out using any of the known immunological methods by employing antibodies which have specificity for mitotic cells. Monoclonal antibodies demonstrating such specificity are known and include MPM-2 which was raised against mitotic HeLa cells and recognizes phospho-epitopes that are highly conserved in mitotic proteins of all eukaryotic species. Other examples are the monoclonal antibodies recognizing phospho-epitopes in the paired helical filament proteins (PHF) found in brain tissue of patients suffering from Alzheimer's disease as described in: PCT International Application published Jul. 4, 1996 under No. WO 96/20218; and, Vincent, I. et al. (1996) "Mitotic Mechanisms in Alzheimer's Disease?" The Journal of Cell Biology, 132:413–425. The examples in this specification make use of the antibody TG-3 described in the latter two references, obtained from Albert Einstein College of Medicine of Yeshiva University, Bronx, N.Y.

TG-3 has a high specificity for mitotic cells. When TG-3 is used in the ELISA assay described herein, a very good signal/noise ratio is achieved permitting the ELISA assay to be easily monitored by optical absorbance.

Dying cells exhibit some characteristics which are similar to mitotic cells. TG-3 does not react with dying cells which prevents apoptotic cells from being counted in the assay of this invention. The efficiency of the assay is not affected by the presence of dying cells.

Immunological methods useful for determination of mitotic cells in this assay include any method for determining antibody-antigen binding, including: immunocytochemistry (eg. immunofluorescence), flow cytometry, immunoblotting, and ELISA. Several immunological methods are described in detail in the examples herein as well as in Vincent I. et al. [supra]. Other immunological procedures not described herein are well-known in the art and may be readily adapted for use in this assay. However, high throughput testing of samples may best be achieved by use of ELISA.

METHODS OF SYNTHESIZING GRANULATIMIDE COMPOUNDS

This invention also provides processes for making compounds of Formula I. Various methods may be used, including syntheses as provided in the examples; isolation from natural sources; coupling of two compounds to produce a didemnimide followed by a cyclization step; etc. For example, one synthesis scheme starts with an appropriately protected indole compound such as indole-3-acetamide and proceeds over essentially two coupling steps to produce a didemnimide type compound, following by a cyclization step. The process may optionally comprise one or more subsequent steps to provide particular substituents required to produce a particular compound of Formula I.

An exemplary synthetic process is as follows, where $P_1$, $P_2$ and $P_3$ are suitable protecting groups. The starting indole compound (appropriately substituted by R and or Z) may be made by methods known in the art.

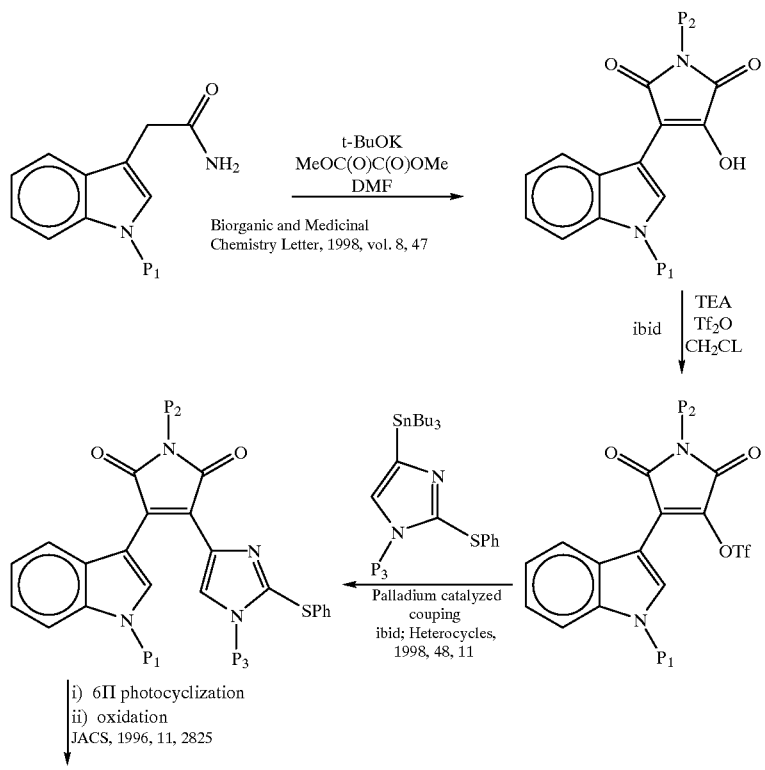

-continued

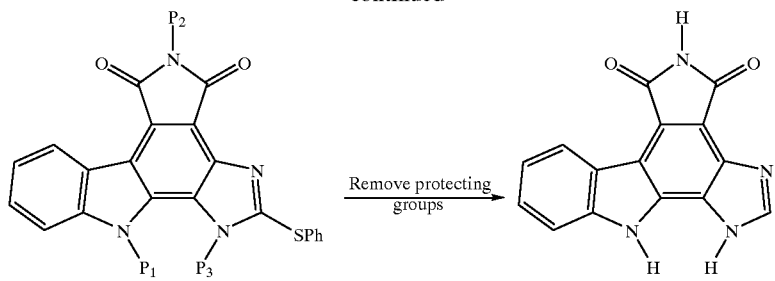

An alternative synthesis scheme, outlined below, involves essentially a single coupling step to produce a didemnimide compound followed by cyclization to produce a compound of Formula I, wherein F, F', X and Y are as defined for Formula I, and W is as defined for Formula I joined to the reactant at (a) and not (b):

granulatimide (typically produced in about 9:1 ratio); as described below. Compound 8 may be produced as described in the examples below. With this embodiment of the preferred synthesis scheme, condensation of 8 with the indole-3-acetamide (9) should be carried out in the presence of molecular sieves, otherwise a second major product

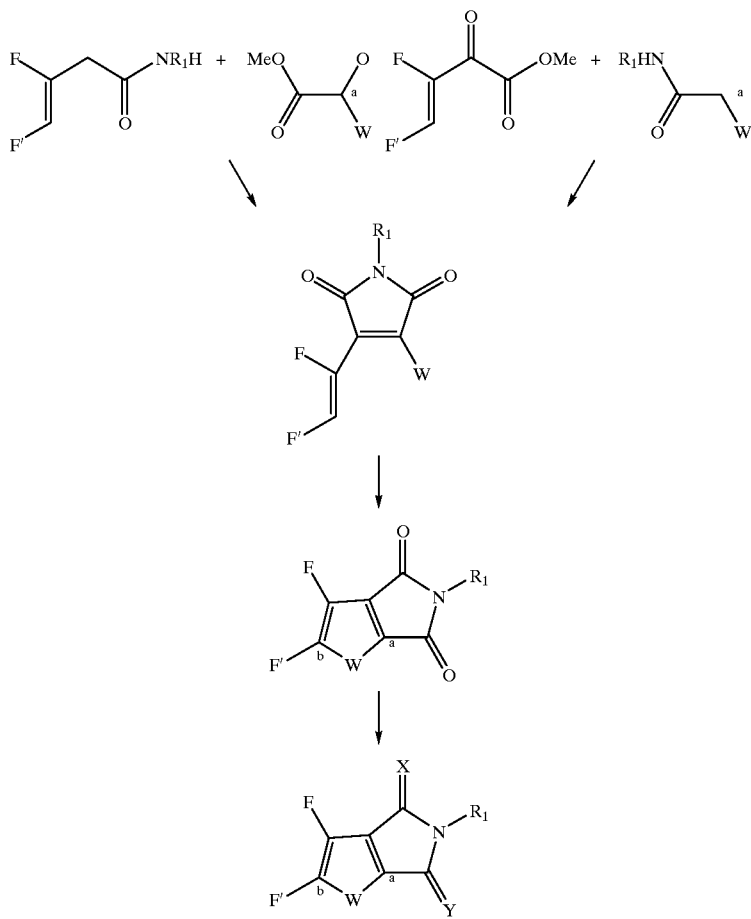

The above-described preferred synthesis scheme is adapted for production of granulatimid end isoresults from displacement of the phenylthio group on (10) by a methoxyl moiety.

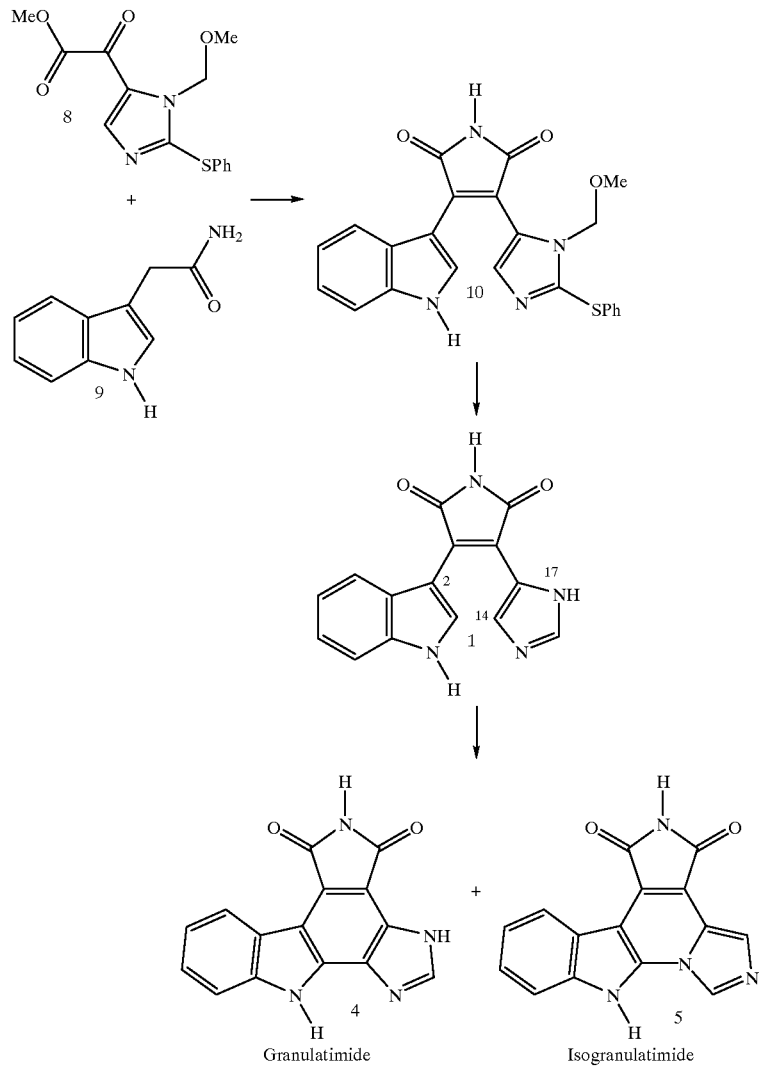

Alternatively, compounds of Formula I can be produced from granulatimide or iso-granulatimide which may be synthesized as described above or obtained from natural sources as described in the Examples. The following schematic describes modification of granulatimide to produce derivatives having different X and Y substituents. The ratio of II to III will be dictated by the choice of protecting groups $P_1$, and $P_2$ or $P_3$, which may be (for example) Cbz, R or H. A protecting group will be used at either $P_2$ or $P_3$, depending upon the position of the double bond in the ring. The chemistry is described in Link, et al. (1996) J. American Chemical Society 118:2825, at p. 2832.

All Z and R groups can be added to aromatic carbons in W and $Ar_1$ prior to the coupling step to prepare the maleimide intermediates. All R, RCO, $Ar_2CO$, and $Ar_2CH_2$ groups can be added to nitrogen atoms using base and an appropriate alkyl halide (RX), acyl halide (RCOX), anhydride ($(RCO)_2O$) or benzyl halide ($Ar_2CH_2X$).

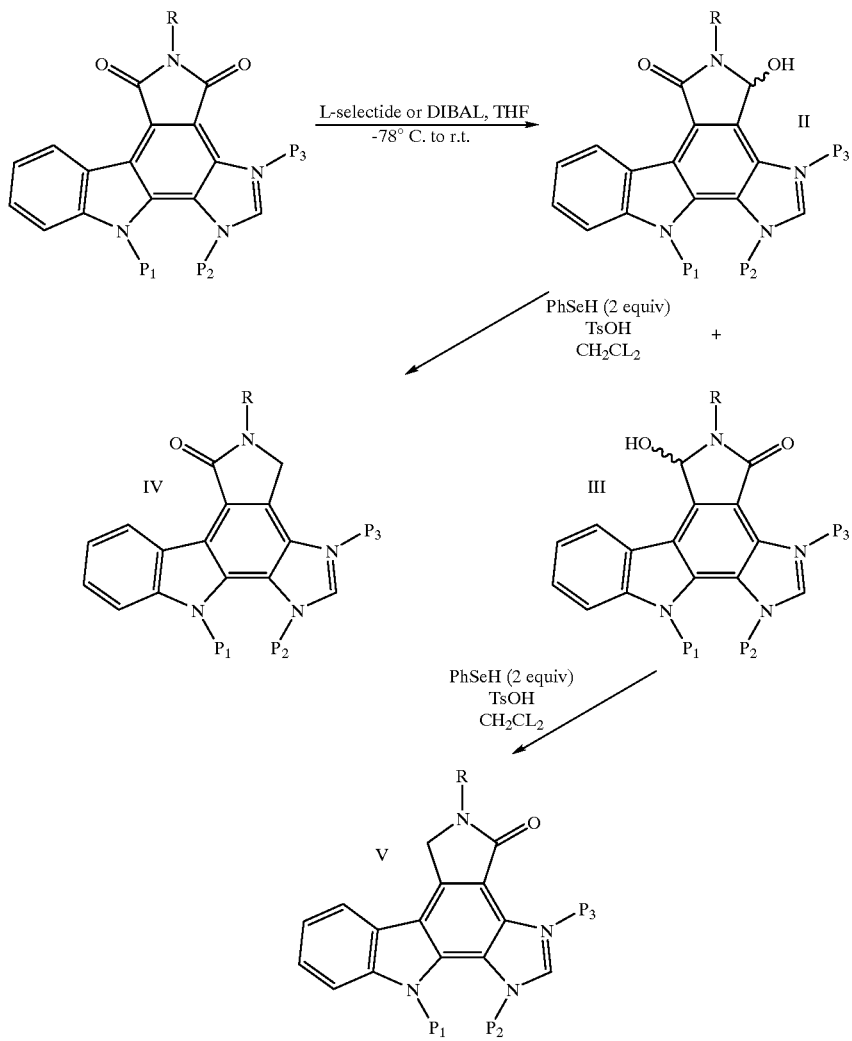

Pharmaceutical Formulations

The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

In pharmaceutical dosage forms, the compounds may be administered in the form of their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing granulatimide compounds is placed in proximity to the site of the tumor, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The combined use of granulatimide compounds and other cytotoxic agents has the advantages that the required dosages for the individual drugs is lower, and the effect of the different drugs complementary. Depending on the patient and condition being treated and on the administration route, the granulatimide compounds may be administered in dosages of 0.1 $\mu$g to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus for example oral dosages in the rat may be ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, the granulatimide compounds may be formulated with other pharmaceutically active agents, particularly other anti-metastatic, anti-tumor or anti-angiogenic agents. Angiostatic compounds of interest include angiostatin, endostatin, carboxy terminal peptides of collagen alpha (XV), etc. Cytotoxic and cytostatic agents of interest include adriamycin, alkeran, Ara-C, BICNU, busulfan, CNNU, cisplatinum, cytoxan, daunorubicin, DTIC, 5-FU, hydrea, ifosfamide, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc.

METHODS OF USE

The subject granulatimide compounds are administered to a subject having undesirable kinase activity, or conditions resulting therefrom. The compounds may also be administered to a subject in order to inhibit the G2 checkpoint, particularly in association with treatment of cancer cells, more particularly in combination with cytotoxic therapy directed at said cancer cells; e.g. radiation treatment, chemotherapeutic drugs, etc.

The host, or patient, may be from any mammalian species, e.g. primate sp., particularly humans; rodents, including mice, rats and hamsters; rabbits; equines, bovines, canines, felines; etc. Animal models are of interest for experimental investigations, providing a model for treatment of human disease.

Tumors known to be susceptible to DNA damaging agents include carcinomas, e.g. colon, prostate, breast, ductal, endometrial, stomach, dysplastic oral mucosa, invasive oral cancer, non-small cell lung carcinoma, transitional and squamous cell, urinary carcinoma, etc.; neurological malignancies, e.g. neuroblastoma, gliomas, etc.; hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-ell rich cutaneous lymphoid hyperplasia, bullous pemphigoid, discoid lupus erythematosus, lichen planus, etc.; and the like.

A combined therapy of granulatimide compounds and cytotoxic agents are administered to a host suffering from a susceptible tumor. Administration may be topical, localized or systemic, depending on the specific disease. The compounds are administered at a combined effective dosage that over a suitable period of time substantially reduces the tumor cell burden, while minimizing any side-effects, usually killing at least about 25% of the tumor cells present, more usually at least about 50% killing, and may be about 90% or greater of the tumor cells present. It is contemplated that the composition will be obtained and used under the guidance of a physician for in vivo use. To provide the synergistic effect of a combined therapy, the active agents can be delivered together or separately, and simultaneously or at different times within the day.

The susceptibility of a particular tumor cell to killing with the combined therapy may be determined by in vitro testing. Typically a culture of the tumor cell is combined with a combination of a cytotoxic compound and a granulatimide compound at varying concentrations for a period of time sufficient to allow the active agents to induce cell death, usually between about one hour and one week. For in vitro testing, cultured cells from a biopsy sample of the tumor may be used. The viable cells left after treatment are then counted.

The dose will vary depending on the specific cytotoxic agent utilized, type of tumor, patient status, etc., at a dose sufficient to substantially ablate the tumor cell population, while maintaining patient viability. In some cases therapy may be combined with stem cell replacement therapy to reconstitute the patient hematopoietic function. Treatment will generally be continued until there is a substantial reduction, e.g. at least about 50%, decrease in the tumor burden, and may be continued until there are essentially no tumor cells detected in the body.

All publications mentioned herein are incorporated herein by reference for the purpose of describing and disclosing, for example, the compounds and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1
G2 Checkpoint Inhibition Assay

MCF-7 mp53 cells (mutant for p53) were cultured as monolayers in DMEM supplemented with 10% fetal bovine serum, 2 mM L-glutamine, 50 units/ml penicillin, 50 $\mu$g/ml streptomycin, 1 mM sodium pyruvate, MEM non-essential amino acids, 1 $\mu$g/ml bovine insulin 1 $\mu$g/ml hydrocortisone, 1 ng/ml human epidermal growth factor, and 1 ng/ml β-estradiol at 37° C. in humidified 5% $CO_2$. The cells were seeded at 10,000 cells per well of 96-well polystyrene tissue culture plates (Falcon) in 100 $\mu$l medium. The cells were allowed to grow for 24 hours and then were irradiated with 6.5 Gy using a $^{60}$Co source (Gammacell 200™, Atomic Energy Commission of Canada) delivering γ-rays at a dose rate of 1.4 Gy/min.

Extracts from marine organisms at about 10 $\mu$g/ml (from 1 000-fold stocks in DMSO) and 100 ng/ml nocodazole (Sigma, from a 1 000-fold stock in DMSO) were added 16 hours after irradiation and the cells were incubated for a further 8 hours. Caffeine at 2 mM (Sigma, from a 100 mM solution in phosphate-buffered saline) was used as a positive control.

After drug treatment, the cell culture medium was removed and the cells were lysed by adding 100 $\mu$l of ice-cold lysis buffer (1 mM EGTA pH 7.4, 0.2 mM PMSF) and pipeting up-and-down 10 times. The cell lysates were transferred to 96well PolySorp™ plates (Nunc) and dried completely by blowing warm air at about 37° C. with a hair dryer positioned about 3 feet above plates. Protein binding sites were blocked by adding 200 $\mu$l per well of antibody buffer (10 mM Tris HCl pH 7.4, 150 mM NaCl, 0.1 mM PMSF, 3% (w/v) dried non-fat milk (Carnation)) for 1 hour at room temperature. This was removed and replaced with 100 $\mu$l antibody buffer containing 0.1–0.15 $\mu$g/ml TG-3 monoclonal antibody and horseradish peroxidase-labelled goat anti-mouse IgM (Southern Biotechnology Associates) at a dilution of 1/500.

After overnight incubation at 4° C., the antibody solution was removed and the wells were rinsed 3 times with 200 l 10 mM Tris HCl pH 7.4, 0.02% Tween 20™. 100 $\mu$l of 120 mM $Na_2HPO_4$, 100 mM citric acid, pH 4.0 containing 0.5 mg/ml 2,2'-azino-bis (3-ethylbenzthiazoline6-sulfonic acid) and 0.01% hydrogen peroxide was added for 1 hour at room temperature and the plates were read at 405 nm using a BioTek™ plate reader. Positive controls treated with 2 mM caffeine gave absorbance readings of about 1.0.

G2 checkpoint inhibition was detected in extracts from the ascidian Didemnum granulatum (Subphylum Urochordata, Class Ascidiacea) collected from rocky, shallow water marine habitats along the coastline of southern Brazil.

Collection and Extraction of D. Granulatum

Didemnum granulatum (85 g wet wt.) was collected during the summer of 1995 at depths of 1 m at the rocky shore of Araca beach, Sao Sebastiao (Sao Paulo state, southeastern Brazil). A second collection was made at the Arquipelago do Arvoredo (Santa Catarina state, southern Brazil, 150 g wet wt.) and in the Sao Sebastiao Channel (Sao Paulo state, 185 g wet wt.) during November 1997. Freshly collected animals were stored in ethanol at −20° C. Animals obtained from the different collections were processed separately as follows: after decantation of ethanol, the animal was blended and extracted three times with methanol. The ethanol and methanol extracts were combined, filtered and evaporated in vacuo to give a gummy residue. The bulk of the residue was dissolved in 8:2 MeOH—$CH_2Cl_2$ and filtered for elimination of inorganic salts while small amounts of the residue were dissolved in DMSO for use in the G2 checkpoint inhibition assay described above.

Isolation of Active Compounds

Methanol extracts from the Brazilian ascidian D. granulatum were fractionated by gel filtration on Sephadex LH-20 (elutent: MeOH) followed by reversed phase HPLC (eluent acetonitrile/0.05% trifluoroacetic acid (1:1)) affording a series of eight fractions having different constituents by TLC. Only one fraction exhibited G2 checkpoint inhibition activity, which provided the novel alkaloid compounds later termed iso-granulatimidend granulatimide. Other fractions contained various forms of the alkaloid didemnimide which were inactive. Didemnimide A and D were identified by comparison of NMR and MS data with literature values (Vervoort, H. C. et al. [supra]).

NMR experiments using a compound isolated from the active fraction identified a disubstituted imidazole moiety. The compound differed from Didemnimide A by the loss of two hydrogen atoms. This led to the conclusion that the new compound has a bond between C-2 of the indole and ether C-14 or N-1 7 of the imidazole fragment of Didemnimide A. The presence of an anisoptropic effect in the novel compound and not in didemnimide A indicated a rigid planar heterocycle, unlike didemnimide A in which the indole and maleimide rings are twisted relative to each other along the C-3 to C-8 bond. The heterocyclic aromatic core of the novel compound is without precedent in natural products.

Characterization of Iso-Granulatimidend Granulatimide

NMR data were collected on Bruker WH 400 (1H NMR, COSY and NOE), AM 400 ($^{13}$C NMR) and AMX 500 (HMBC and HMQC) spectrometers. Proton spectra were referenced using the internal residual signal of DMSO-d$_5$ (δ2.49) and carbon spectra were referenced to the DMSO methyl resonance (δ39.5). FABMS data were collected on a Kratos concept IIHQ hybrid mass spectrometer with cesium ion secondary ionization and magnetic sector mass analyzer. Samples were dissolved in a MeOH-thioglycerol matrix, and spectra were obtained using a source voltage of 8 kV and a cesium ion gun voltage of 12 kV. Infrared spectra were recorded on a Perkin Elmer 1710 spectrophotometer and UV spectra on a spectrophotometer.

A compound (later termed iso-granulatimide) was isolated from active fraction as a red amorphous solid (UV ($\lambda_{max}$nm($\epsilon$)) 210 (10,200), 231 (10,600) 280 (6,550), 470 (1,870)) that gave a [M+H]+ion at m/z 277.0730 in the HRFABMS appropriate for a molecular formula of $C_{15}H_8N_4O_2$ (calculated mass for $C_{15}H_8N_4O_2$, 277.0714). An NH proton resonance at δ11.11 showed HMBC correlations to carbonyl resonances at δ169.8 and 168.8 and aromatic carbon resonances at δ126.39 and 112.22, confirming the presence of a maleimide substructure. The COSY spectrum identified a four proton spin system (δ8.51, d, J=7 Hz (H-4)); 7.43, dd, J=7,7 Hz (H-6); 7.35, dd, J=7,7 Hz (H-5); 7.67 d, J=7 (H-7) that may be assigned to the H-4 to H-7 protons of an indole residue. Irradiation of a broad proton resonance at δ 13.48 induces an NOE only in the aromatic doublet at δ7.68, which assigns the doublet to H-7 and the broad proton resonance to the indole NH. The absence of a resonance in the 1H NMR spectrum of the compound that may be assigned to the indole H-2 or H-3 protons indicated the presence of substituents at C-2 and C-3.

Very broad resonances at δ8.10 and δ9.12 in the 1H NMR spectrum were assigned to the imidazole moiety. The broadness of the imidazole resonances was attributed to tautomeric equilibrium of the NH protons The large chemical shift observed for the H-4 resonance (δ8.51) in the new compound relative to the chemical shift observed for the H-4 resonance in didemnimide A (δ7.07) was attributed to a neighbouring group effect from a C-9 maleimide carbonyl.

As described above, the new compound was predicted to be a polycyclic aromatic differing from didemnimide A by the presence of a bond between the C-2 carbon of the indole fragment and either C-14 or N-17 of the imidazole fragment. In the former case, the compound would be granulatimide as described herein and in the latter case, iso-granulatimide. The broadness of the imidazole resonances in the NMR spectra initially made use of NMR ineffective in distinguishing the two compounds. Therefore, both granulatimide and iso-granulatimide were synthesized as described herein and compared to the compound derived from the natural source which revealed the compound to be iso-granulatimide. TLC analysis (CH2C12—MeOH 9:1; UV at 254 nm) of pooled active fractions from the natural extract using synthetic granulatimides a reference revealed presence of the latter compound in an amount substantially less than iso-granulatimide. However, it was determined that the synthetic granulatimide is very insoluble in most common organic solvents including ethanol and methanol and was therefore not efficiently extracted from the natural source in the procedure described above.

Granulatimide is soluble in DMF or DMSO and one of the latter solvents is recommended for extraction of granulatimide from the natural source.

Table 1 provides comparative 1H-NMR data determined using synthetic compounds as recorded in DMSO-d6.

TABLE 1

| Atom No. | Granulatimide (4) | Isogranulatimide (5) |
|---|---|---|
| 1 | 12.58, bs | 13.48, bs |
| 2 | — | — |
| 4 | 8.89, d, J=7Hz | 8.51, d, J=7Hz |
| 5 | 7.30, dd ,J=7, 7Hz | 7.35, dd, J=7, 7Hz |
| 6 | 7.48, dd, J=7, 7Hz | 7.43, dd, J=7, 7Hz |
| 7 | 7.61, d, J=7Hz | 7.67, d, J=7Hz |
| 10 | 10.96, s | 11.11, bs |
| 14 | — | 8.10, b |
| 16 | 8.50, s | 9.12, b |
| 17 | 13.57, s | — |
| 18 | — | — |

Activity of Iso-Granulatimid and Granulatimide

Iso-granulatimide shows half-maximal G2 checkpoint inhibition (IC50) at 1.8±0.2 μM (FIG. 1A). Didemnimide A shows no activity at concentration of 0.1–30 μM). Iso-granulatimide shows mild cytotoxicity, with an IC50 of 40±4 μM (FIG. 1B, curve 0 Gy), well above the IC50 for checkpoint inhibition.

G2 checkpoint inhibitors and DNA-damaging agents would be expected to kill p53-cells synergistically. When such cells were exposed to 2, 4 or 6 Gy of γ-irradiation and to different concentrations of iso-granulatimide for 16 hours, cells died in higher numbers than for the sum of each treatment alone (FIG. 1B), showing that γ-irradiation and granulatimidectoide synergistically.

The IC50 for cytotoxicity of iso-granulatimide was reduced by 5-fold when cells were irradiated with 6 Gy (FIG. 1B). By comparison, caffeine, the most commonly used G2 checkpoint inhibitor, exhibits an IC50 of 1 mM for G2 checkpoint inhibition, has very little cytotoxicity alone and also acts synergistically with γ-irradiation.

Irradiation with iso-granulatimide treatment does not kill p53+ cells synergistically, as shown in FIG. 1C. Therefore, the iso-granulatimide preferentially kills irradiated p53− (tumour) cells over irradiated p53+ (normal) cells.

Figure 2:
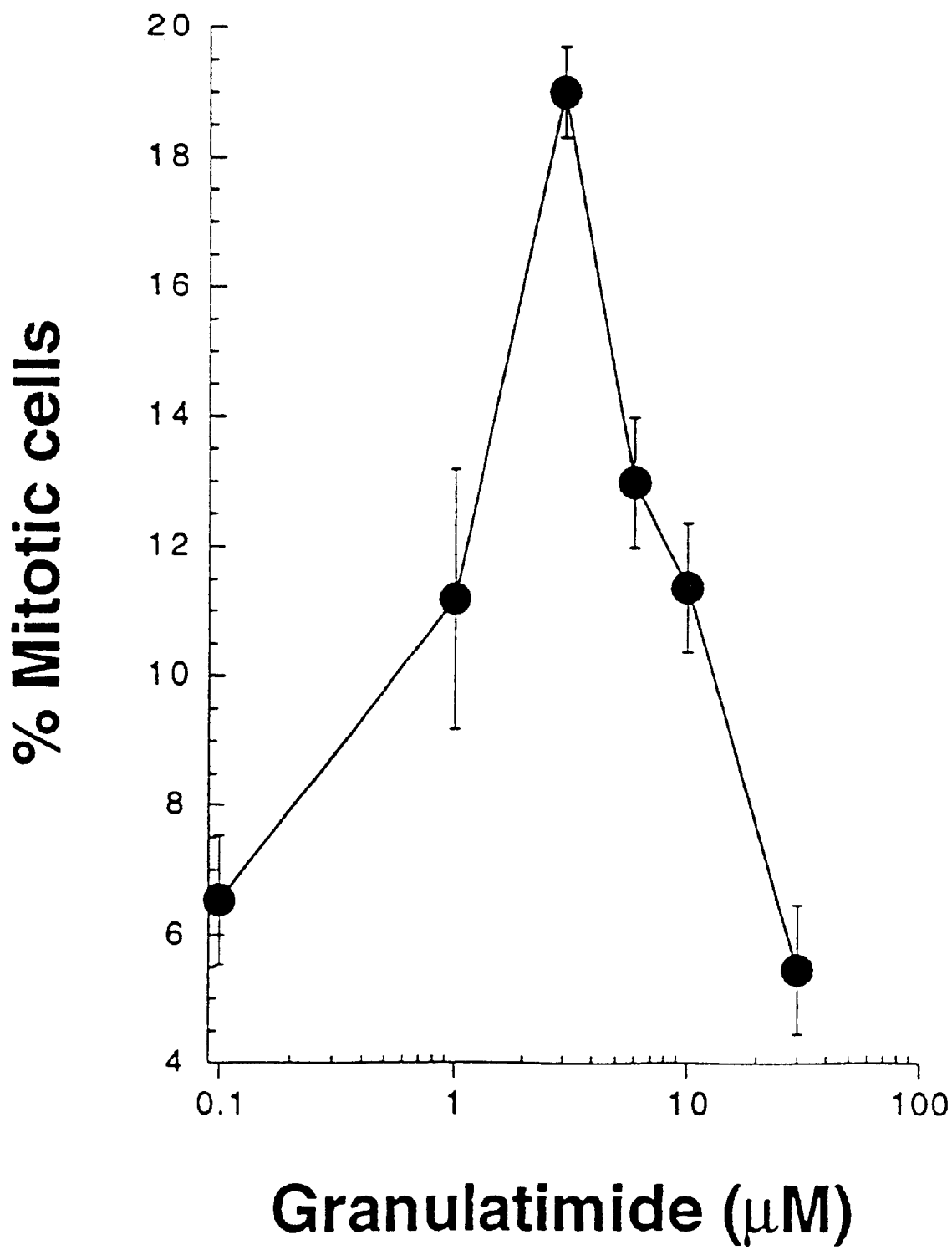
FIG. 2 is a graph showing G2 checkpoint inhibition on by granulatimide.

As is shown in FIG. 2, granulatimide may be more potent as a G2 checkpoint inhibitor (IC50=1.3 μm) as compared to iso-granulatimide.

Example 2

Synthesis of Iso-Granulatimide and Granulatimide

Throughout these examples, TLC was carried out by using commercial aluminum-backed silica gel 60 plates. Flash chromatography was carried out with 230–400 mesh silica gel (E. Merck). THF was distilled from sodium/benzophenone and CH2Cl2 was distilled from CaH2. Commercial EtOH (reagent grade) and MeCN (HPLC grade) were used without further purification. Molecular sieves were dried under vacuum with heating for 5 hours prior to use. All reactions were carried out under an atmosphere of dry argon using glassware that had been thoroughly flame dried.

Methyl 2-(1-methoxymethyl-2phenylthioimidazol-5yl) glyoxylate (8). To a cold (−78° C.), stirred solution of 1-methoxymethyl-2phenylthioimidazole (Ohta, S. et al. (1992) Chem. Pharm. Bull. 40:2681) (11) 340 mg, 1.55 mmol) in dry THF (8.0 mL) was added a solution of n-BuLi (1.47 M in hexanes, 1.26 mL, 1.85 mmol) and the mixture was stirred for 1 hour. A solution of dimethyl oxalate (540 mg. 4.58 mmol) in dry THF (2.0 mL) was added and the mixture was stirred at −78° C. for an additional 1.25 hours. The reaction mixture was treated with saturated aqueous NH₄Cl (5.0 mL) and Et2O (20 mL). The phases were separated and the aqueous layer was extracted with Et2O (25 mL). The combined organic extracts were washed (brine, 10 mL), dried (MgSO₄), and concentrated. Flash chromatography (35 g of silica gel, 1:1 petroleum ether-Et2O) of the crude material afforded 305 mg (66%) of 8 as a beige solid that exhibited mp 59–60° C.; IR (KBr) 1729, 1657, 1305, 1273, 1167, 1114, 784 cm−1; 1H NMR (CDCl3, 400 MHz) δ8.23 (s, 1H), 7.52–7.54 (m. 2H), 7.37–7.38 (m, 3H), 5.81 (s, 2H), 3.91 (s, 3H), 3.36 (s, 3H); 13C NMR (CDCl3, 100 MHz) δ172.2, 161.6, 154.1, 145.4, 145.3, 133.2, 129.5, 129.2, 128.7, 75.8, 56.5, 53.0; HREIMS calcd for C14H14N2O4'S 306.0674, found 306.0674.

3-[4-(1-methoxymethyl-1H-2-phenylthioimidazol-5yl)-2, 5-dioxo-2, 5-dihydro-1H-pyrrol-3-yl]-indole (10).

To a stirred solution of t-BuOK (50 mg, 0.45 mmol) in DMF (2.0 mL) at room temperature was added sequentially 4Å molecular sieves (~200 mg) and a solution of 8 (56 mg, 0.18 mmol) and indole-3-acetamide (9) (38 mg, 0.22 mmol) in DMF (3.0 mL) the reaction mixture was heated to 45° C. and stirred for 12 hours. The dark purple solution was treated with hydrochloric acid (1 N, 1.5 mL) and EtOAc 10 mL). The phases were separated and the aqueous layer was extracted with EtOAc (2×10 mL). The combined organic extracts were washed (brine 4×10 mL), dried (MgSO4), and concentrated. Flash chromatography (12 g of silica gel, 30:1 CH2Cl12—MeOH) of the crude material afforded 249 mg (93%) of 10 as an orange solid that exhibited mp 243° C. ; IR (KBr) 3400–2600, 1765, 1708, 1537,1341, 741 cm−1; 1H NMR (400 MHz) δ12.11 (br s, 1H), 11.25 (br s, 1H), 8.14 (s, 1H) 7.46 (d, 1H, J=7.9 Hz), 7.18–7.33 (m, 6H), 7.14 (poorly resolved dd, 1H), 6.77 (poorly resolved dd, 1H), 6.51 (d, 1H, J=8.0), 500 (s, 2H), 2.97 (s, 3H); 13C NMR (100 MHz) δ171.7, 171.6, 140.3, 136.7, 135.3, 133.8, 133.5, 132.5,129.5, 128.4,127.2, 125.7, 124.3, 122.7, 120.8, 120.2, 117.4,112.6, 104.6, 75.8, 55.9; HREIMS calcd for C23H18N4O3S 430.1099, found 430.1099.

3-[4(3-methoxymethyl-3H-imidazol-4-yl)-2,5-dioxo-2,5-dihydro-1H-pyrrol-3-yl]-indole (12)

To a refluxing solution of 10 (52 mg, 0.12 mmol) in EtOH (5.0 mL) was added Raney Ni (W-2, ~150 mg) and the suspension was refluxed for 1 hour. An additional amount of Raney Ni (W-2,-100 mg) was added and the mixture was refluxed for an additional 3 hours. The reaction mixture was then cooled to room temperature and filtered through Celite. The Celite was washed with CH₂Cl₂—MeOH (1:1, 75 mL) and the combined organic washed were concentrated. Flash chromatography (14 g of silica gel, 20:1 CH₂Cl₂—MeOH) of the crude material afforded 33 mg (85%) of 12 as an orange solid: m.p.>235° C., dec.; IR (KBr) 3400–2600, 1765, 1703, 1537, 1440, 1342, 1113, cm−1; 1H NMR (400 MHz) 67 10.89 (br s, 1H), 10.03 (br s, 1H), 8,07 (s, 1H), 7.94 (s, 1H), 7.44 (d, 1H, J=8.5 Hz), 7.09 (poorly resolved dd, 1H), 7.0 (s, 1H), 6.8 (poorly resolved dd, 1H), 6.46 (d, 1H, J=8.0 Hz), 5.02 (s, 2H), 3.07 (s, 3H); $^{13}$C NMR (100 MHz) δ171.8, 171.7, 140.5,136.5, 134.3, 132.9, 131.8, 124.3, 122.4, 121.7, 120.5, 120.3, 118.4, 112.3, 104.7, 76.4, 55.6; HREIMS calcd for C17H14N4O3 322.1066, found 322.1066.

Synthesis of Didemnimide A (1)

To a stirred suspension of 12 (32.4 mg, 0.1 mmol) in CH₂Cl₂ (10.0 mL) at room temperature was added a solution of BBr₃ in CH₂Cl₂ (1.0 M, 2.5 mL, 25 mmol) and the deep blue solution was stirred for 12 hours. The mixture was treated with saturated aqueous NaHCO₃ (5 mL) and EtOAc (20 mL) and then was stirred for 0.25 hours. The phases were separated and the aqueous layer was extracted with EtOAc (2×15 mL). The combined organic extracts were washed (brine, 10 mL), dried (MgSO₄) and concentrated. Flash chromatography (10 g of silica gel, 15:1 CH2Cl12—MeOH) of the crude material afforded 12.3 mg of recovered 12 as well as 14.9 mg (54%, 86% based on recovered starting material) of 1 as an orange solid 1H NMR (400 MHZ, major tautomer) δ12.45 (br s, 1H), 11.66 (br s, 1H), 10,87 (br s, 1H), 8.05 (s, 1H), 7.71 (br s, 1H), 7.68 (br s, 1H), 7.39 (br d, 1H, J=7.8 Hz), 7.07 (br m, 2H), 6.87 (br m, 1H); 13C NMR (100 MHz) δ172.8, 172.6, 136.1, 135.9, 130.9, 130.5, 126.0, 126.0, 121.7, 121.3, 119.7, 119.2, 112.2, 111.5, 105.0; HREIMS cald for C15H10N4O2 278.0804, found 278.0804.

Granulatimide (4) and Iso-granulatimide (5). To a solution of 1 (12.9 mg, 0.046 mmol) in MeCN (5.0 mL) was added a catalytic amount of palladium-on-carbon (10% Pd) and the resulting mixture was sparged with argon for 0.5 hours. The mixture was irradiated (450 Watt Hanovia medium pressure mercury vapour lamp, quartz reaction vessel) for 6.5 hours. The reaction mixture was filtered through Celite, the Celite was washed with DMF (10 mL), and the combined filtrate was concentrated. The remaining material was taken up in EtOAc (30 mL) and the resultant solution was washed (brine, 4×20 mL), dried (MgSO₄) and concentrated. Flash chromatography (20 g of silica gel, 10:1 CH2Cl12—MeOH) of the crude material afforded 11.7 mg (91%) of 4 as a yellow solid and 1.0 mg (8%) of 5 as a red solid. Final purification was achieved on RPHPLC (1:1 CH3CN-0.05% TFA). Granulatimide (4): 1H NMR (400 MHz) see Table 1; UV (MeOH) 230, 270, 285, 295, and 380 nm; HREIMS calcd for C15H8N4O2 276.0647, found 276.0652. Iso-granulatimide (5): See above and Table 1.

Example 3

Alternative Synthesis of Iso-granulatimide (5)

Method A: To a stirred solution of didemnimide A (32.6 mg, 0.117 mmol) in 2-butanone (7.0 mL) at rt is added sequentially 4Å molecular sieves (~100 mg) and CUCl₂ (79 mg, 0.59 mmol). The reaction mixture was stirred for 15 h at rt. The dark purple solution was treated with 10% solution of NaOH until the pH was neutral and diluted with EtOAc (30 mL). The phases were separated and the aqueous layer was extracted with EtOAc (5×10 mL). The combined organic extracts were washed with brine (10 mL), dried (MgSO₄) and concentrated. Flash chromatography (15 g of silica gel, 15:1 CH₂Cl₂—MeOH) of the crude material afforded 19.5 mg (60%) of recovered didemnamide A as well as 12.3 mg (38%, 95% based on recovered starting material) of iso-granulatimide (5) as a purple solid.

Method B: A stirred solution of didemnimide A (14.7 mg, 0.053 mmol) in DMSO (5.0 mL) was heated to 160 ° C. for 1 h. The reaction mixture was cooled to rt, diluted with EtOAc (30 mL), washed with brine (3×10 mL), dried (MgSO₄), and concentrated. Flash chromatography (25 g of silica gel, 10:1 CH₂Cl₂—MeOH) of the crude material afforded 12.4 mg (85%) of isogranulatimide (5) as a purple solid; IR (KBr) 2732, 1758, 1719, 1586, 1568, 1368, 1234, 1109, 744 cm$^{−1}$; $^1$H NMR (400 MHz) 13.39 (bs, 1H), 11.09 (bs, 1H), 8.84 (s, 1H), 8.44 (d, 1 H, J=7.6 Hz), 7.82 (s, 1H), 7.62 (d, 1H, J=8.0 Hz), 7.40 (dd, 1H, J=8,8 Hz), 7.31 (dd, 1H, J=8,8 Hz); $^{13}$C NMR (100 MHz) 169.9, 169.0, 135.6, 134.9, 126.9, 124.7, 123.1, 122.3, 121.8, 121.3, 121.0, 113.9, 112.3, 97.6; HREIMS calcd for C₁₅H₈N₄O₂ 276.0647, found 276.0647

Example 4

Synthesis of Granulatimide Compounds

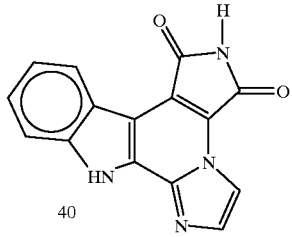

40

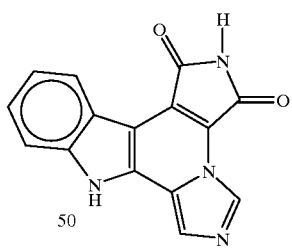

50

Retro Synthesis

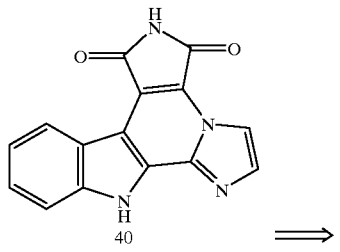

40

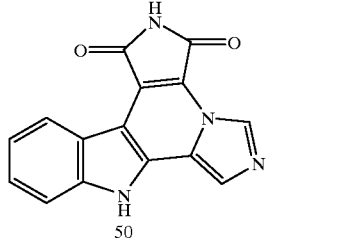

50

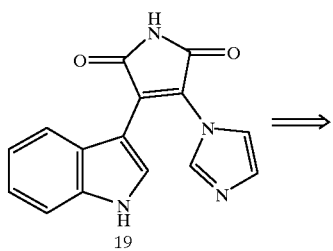

19

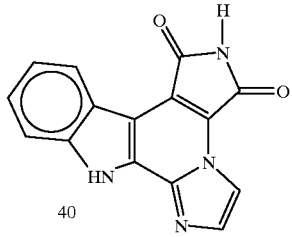

20

+

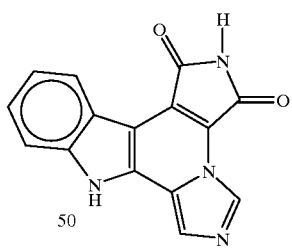

21

Imidazol-1H-1-acetamide (20) To a stirred suspension of NaH (60% dispersion in oil, 352 mg, 8.80 mmol) in DMF (5.0 mL) at 0° C. was added a solution of imidazole (536 mg, 8.00 mmol) in DMF (10.0 mL). The reaction mixture was warmed to rt and stirred for 0.5 h. The reaction mixture was then cooled to 0° C. and iodoacetamide (1.63 g, 8.81 mmol) was added in one portion. The resultant mixture was then warmed to rt and stirred for an additional 1.5 h. The reaction mixture was diluted with $CH_2Cl_2$ (20 mL) and NaI crystals were removed by filtration. The mother liquor concentrated and placed on a neutral alumina column (40 g) and eluted with $CH_2Cl_2$—MeOH (6:1), and concentrated. Flash chromatography (60 g of silica gel, 7:1 $CH_2Cl_2$—MeOH) of the crude material afforded 747 mg (75%) of 20 as a white solid that exhibited mp 185–186° C. (lit. 182–183° C.)#; IR (KBr) 3349, 3116, 1685, 1516, 1408, 1312, 1236, 1080, 750, 663 $cm^{-1}$; $^1H$ NMR (400 MHz) δ7.54 (s, 1H), 7.51 (bs, 1H), 7.20 (bs, 1H), 7.06 (s, 1H), 6.84 (s, 1H), 4.61 (s, 2H); $^{13}C$ NMR (100 MHz) δ168.5, 138.0, 127.5, 120.4, 48.4; HREIMS calcd for $C_5H_7N_3O$ 125.0589, found 125.0589.

Methyl Indolyl-3glyoxylate (21) To a cold (0° C.) stirred solution of 3-indoleglyoxylic acid (1.00 g, 5.29 mmol) in MeOH (10.0 mL) and benzene (40.0 mL) was added (trimethylsilyl)diazomethane (2.0 M in hexanes, 5.3 mL, 10.6 mmol) and the mixture was warmed to rt and stirred for 4 h. The solvent was removed under vacuo to provide a beige solid. Flash chromatography (80 g of silica gel, 25:1 then 10:1 $CH_2Cl_2$—MeOH) of the crude material afforded 990 mg (92%) of 21 as a beige solid that exhibited: $^1H$ NMR (400 MHz) 12.40 (bs, 1H), 8.44 (d, 1H, J=3.0 Hz), 8.15 (d, 1H, J=7.0 Hz), 7.54 (d, 1H, J=7.6 Hz), 7.24-7.31 (m, 2H), 3.88 (s, 3H); $^{13}C$ NMR (100 MHz) 178.7, 163.9, 138.3, 136.7, 125.4, 123.8, 122.8, 121.1, 112.7, 112.4, 52.5; HREIMS calcd for $C_{11}H_9NO_3$ 203.0582, found 203.0582.

3-[4-(1H-imidazol-1-yl)-2,5-dioxo-2,5-dihydro-1H-pyrrol-3-yl]-indole (19) To a stirred solution of t-BuOK (140 mg, 1.25 mmol) in DMF (2.0 mL) at 0° C. was added a solution of 20 (31.1 mg, 0.249 mmol) and methyl indole-3-glyoxylate (21) (101.1 mg, 0.498 mmol) in DMF (3.0 mL). The reaction mixture was stirred for 12 h at rt and then heated to 45° C. for 3 h. The reaction mixture was then cooled and treated with saturated aqueous NH$_4$Cl (5 mL) and EtOAc (20 mL). The phases were separated and the aqueous layer was extracted with EtOAc (2×20 mL). The combined organic extracts were washed with brine (4×10 mL), dried (MgSO$_4$), and concentrated. Flash chromatography (25 g of silica gel, 10:1 then 6:1 CH$_2$Cl$_2$—MeOH) of the crude material afforded 54.5 mg (79%) of 19 as a red solid that exhibited IR (KBr) 3121, 2729, 1767, 1719, 1651, 1495, 1340, 1239, 746 cm$^{-1}$; $^1$H NMR (400 MHz) 10.75 (bs, 1H), 10.00 (bs, 1H), 8.03 (d, 1 H, J=3.1 Hz), 7.78 (s, 1H), 7.48 (d, 1H, J=8.2 Hz), 7.29 (s, 1H), 7.11 (dd, 1H, J=8,8 Hz), 7.04 (s, 1H), 6.80 (dd, 1H, J=8,8 Hz), 6.21 (d, 1H, J=7.6 Hz); $^{13}$C NMR (100 MHz) 170.4, 168.4, 137.8, 136.4, 131.6, 128.8, 125.8, 124.3, 124.1, 122.5, 120.6, 120.1, 119.6, 112.3, 102.3; HREIMS calcd for C$_{15}$H$_{10}$N$_4$O$_2$ 278.0804, found 278.0804.

RB3-195-1 and RB3-195-2 A solution of 19 in t-BuOH and MeCN was sparged with argon for 0.5 h. The yellow mixture was then irradiated (450 Watt Hanovia medium pressure mercury vapour lamp, quartz reaction vessel) for 4 h. The reaction mixture was concentrated and redissolved in acetone (10 mL). To the crude reaction product in acetone at rt was added 10×CuCl$_2$ and the reaction mixture was stirred, exposed to air, overnight. The solvent was then removed in vacuo and the residue was taken up in DMF (10 mL) and filtered through celite. The filtrate was then diluted with EtOAc (50 mL) and washed with brine (4×10 mL), dried (MgSO$_4$), and concentrated to afford 40 and 50 in a 3:1 ratio. Trituration of the crude solid with MeOH afford small amounts of 40 as an insoluble yellow solid; IR (KBr) cm$^{-1}$ 3184, 2931, 2692, 1756, 1718, 1656, 1365, 1309, 1134, 730; $^1$H NMR (400 MHz) 13.14 (bs, 1H), 11.27 (bs, 1H), 8.63 (d, 1 H, J=8.1 Hz), 8.46 (s, 1H), 7.90 (s, 1H), 7.66 (d, 1H, J=8.0 Hz), 7.50 (dd, 1H, J=7,7 Hz), 7.36 (dd, 1H, J=8,8 Hz); HREIMS calcd for C$_{15}$H$_8$N$_4$O$_2$ 276.0647, found 276.0647. Unfortunately the MeOH washes could not be purified to provide significant quantities of 50 or 40. A small amount (approx. 0.5 mg, approx. 70% pure) of 50 was recovered through repeated column chromatographies and submitted for bioassay. Compound 40 was found to be inactive, having an IC50 >100 μM in the G2 assay; while compound 50 was active, having an IC50 of 1 μM.

Example 5

Synthesis of 60

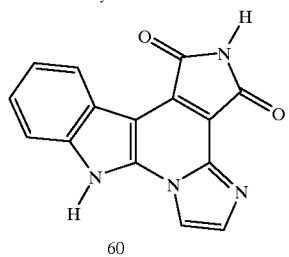

60

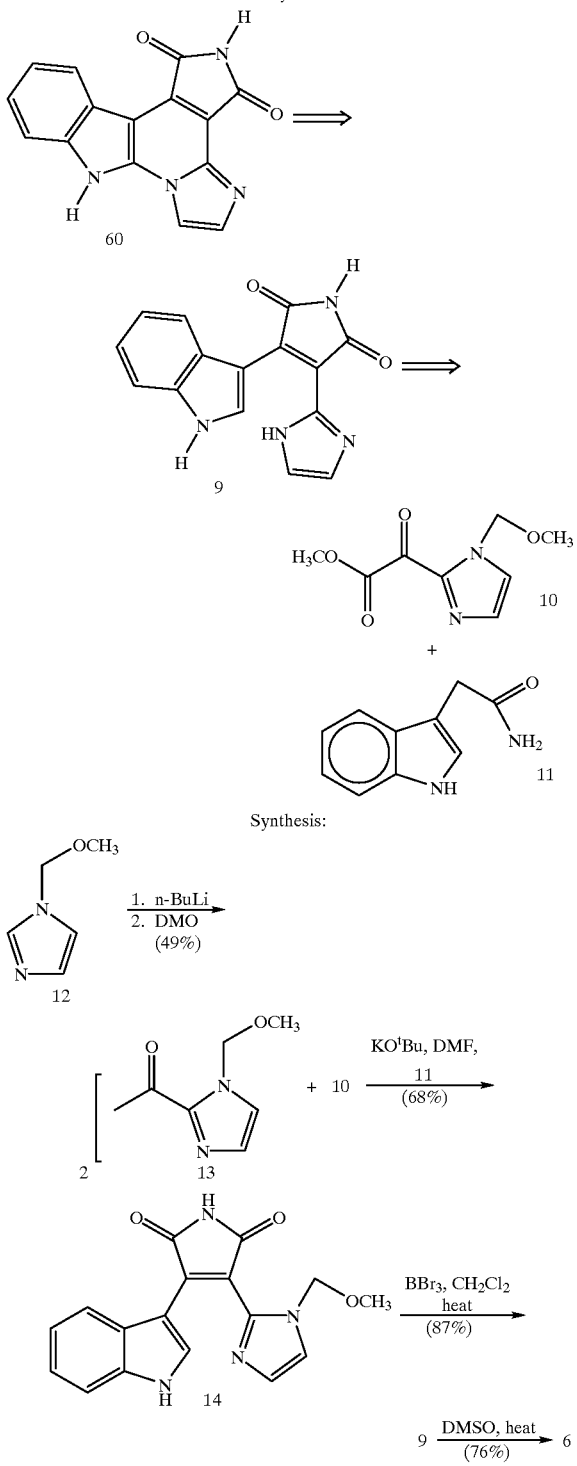

Methyl 2-(1-methoxymethy-1H-limidazol-2-yl) glyoxylate (10) To a cold (−48° C), stirred solution of 1-methoxymethyl-1H-imidazole# (12) (335 mg, 2.99 mmol) in dry THF (15.0 mL) was added a solution of n-BuLi (1.50 M in hexanes, 2.30 mL, 3.45 mmol) and the mixture was stirred for 1 h. The reaction mixture was then cooled to −78° C. and added to a solution of dimethyloxalate (1.17 g, 9.9 mmol) in THF (10.0 mL) at −78° C. the mixture was stirred at −78° C. for an additional 0.33 h. The reaction mixture was treated with saturated aqueous $NH_4Cl$ (5 mL) and EtOAc (15 mL). The phases were separated and the aqueous layer was extracted with EtOAc (2×20 mL). The combined organic extracts were washed with brine (10 mL), dried ($MgSO_4$), and concentrated. Flash chromatography (50 g of silica gel, 50:1 $CH_2Cl_2$—MeOH) of the crude material afforded 290 mg (49%) of 10 as an oil that exhibited IR (KBr) 2957, 1744, 1679, 1412, 1276, 1215, 1109, 1005 cm$^{-1}$; $^1$H NMR (CDCl$_3$, 400 MHz) 7.38 (s, 1H), 7.33 (s,1H), 5.71 (s, 2H), 3.96 (s, 3 H), 3.33 (s, 3H); $^{13}$C NMR (CDCl$_3$, 100 MHz) 177.9, 164.3, 140.6, 132.9, 126.9, 78.8, 57.5, 53.4; HREIMS calcd for $C_8H_{10}N_2O_4$ 198.0641, found 198.0641.

3-[4-(1-methoxymethyl-1H-imidazol-2-yl)-2,5-dioxo-2,5dihydro-1H-pyrrol-3-yl]-indole (14) To a stirred solution of 10 (142.0 mg, 0.717 mmol) and indole acetamide (62.7 mg, 0.360 mmol) in DMF (5.0 mL) was added a solution of t-BuOK (101 mg, 0.902 mmol) in DMF (5.0 mL) at rt. The reaction mixture was stirred overnight at rt then heated to 45° C. and stirred for an additional 20 h. The reaction mixture was then cooled and treated with saturated aqueous $NH_4Cl$ (5 mL) and EtOAc (20 mL). The phases were separated and the aqueous layer was extracted with EtOAc (2×20 mL). The combined organic extracts were washed with brine (4×10 mL), dried ($MgSO_4$), and concentrated. Flash chromatography (40 g of silica gel, 40:1 $CH_2Cl_2$—MeOH) of the crude material afforded 79.1 mg (68%) of 14 as a red solid that exhibited IR (KBr) 2500–3400, 1759, 1713, 1626, 1531, 1341, 1025, 745 cm$^{-1}$; $^1$H NMR (400 MHz) 12.06 (bs, 1H), 11.17 (bs, 1 H), 8.22 (s, 1H), 7.45 (s, 1H), 7.41 (d, 1H, J=7.9 Hz), 7.11 (s, 1H), 7.08 (dd, 1 H, J=8.1 Hz), 6.77 (dd, 1H, J=8,8 Hz), 6.23 (d, 1H, J=8.1 Hz), 5.06 (s, 2H), 3.08 (s, 3H); $^{13}$C NMR (100 MHz) 171.6, 171.4, 138.0, 137.7, 136.6, 132.7, 129.2,124.8, 122.4, 122.0, 120.7, 120.2, 118.1, 112.1,105.1, 76.8, 55.7; HREIMS calcd for $C_{17}H_{14}N_4O_2$ 322.1066, found 322.1066.

3-[4-(1H-imidazol-2-yl)-2,5-dioxo-2,5dihydro-1H-pyrrol-3-yl]indole (9) To a stirred suspension of 14 (18.0 mg, 0.056 mmol) in $CH_2Cl_2$ (5.0 mL) at rt was added BBr$_3$ (1.0 M in $CH_2Cl_2$, 0.56 mL, 0.56 mmol) and the resulting blue mixture was heated under refluxing conditions for 5 h. The reaction mixture was cooled to rt and treated with saturated aqueous $NaHCO_3$ (5 mL) and EtOAc (10 mL) and then stirred for 0.5 h. The phases were separated and the aqueous layer was extracted with EtOAc (3×10 mL). The combined organic extracts were washed with brine (10 mL), dried ($MgSO_4$) and concentrated. Flash chromatography (25 g of silica gel, 20:1 $CH_2Cl_2$—MeOH) of the crude material afforded 13.5 mg (87%) of 9 as a red solid that exhibited IR (KBr) 3385, 3140, 1759, 1709, 1630, 1494, 1431, 1346, 1025, 1002, 747 cm$^{-1}$; $^1$H NMR (major tautomer, 400 MHz) 12.32 (bs, 1 H), 11.90 (bs, 1H), 11.13 (bs, 1H), 8.48 (d, 1H, J=3.2 Hz), 7.43 (d, 1H, J=8.0 Hz), 7.18–7.28 (m, 2H), 7.10 (dd, 1H, J=7,7 Hz), 6.88–6.96 (m, 2H); $^{13}$C NMR (100 MHz) δ172.1, 172.0, 170.2, 137.1, 136.4, 133.0, 132.8, 125.2, 122.0, 121.6, 120.2, 120.0, 119.2, 111.9, 105.0; HREIMS calcd for $C_{15}H_{10}N_4O_2$ 278.0804, found 278.0804.

Iso-iso-granulatimide (60) A stirred solution of 9 (14.4 mg, 0.052 mmol) in DMSO (5 mL) was heated to 120° C. for 8 h. The reaction mixture was cooled to rt, diluted with EtOAc (30 mL), washed with brine (3×10 mL), dried ($MgSO_4$), and concentrated. Flash chromatography (20 g of silica gel, 20:1 then 10:1 $CH_2Cl_2$—MeOH) of the crude material afforded X mg of recovered 9 and 11.0 mg (76%,x% based on recovered starting material) of 60 as an orange solid that exhibited IR (KBr) cm$^{-1}$ 2600–3400, 1755, 1717, 1631, 1591, 1575, 1464, 1376, 1336, 1232, 751; $^1$H NMR (400 MHz) 13.36 (bs, 1H), 11.13 (bs, 1H), 8.63 (d, 1 H, J=7.7 Hz), 8.40 (s, 1H), 7.93 (s, 1H), 7.69 (d, 1H, J=8.2 Hz), 7.48 (dd, 1H, J=7,7 Hz), 7.38 (dd, 1H, J=7,7 Hz); $^{13}$C NMR (100 MHz); HREIMS calcd for $C_{15}H_8N_4O_2$ 276.0647, found 276.0647.

In the G2 checkpoint inhibition assay, compound 60 had an $IC_{50}$ of 2 μM.

Example 6

Synthesis of Cyclodidemnimide C (7)

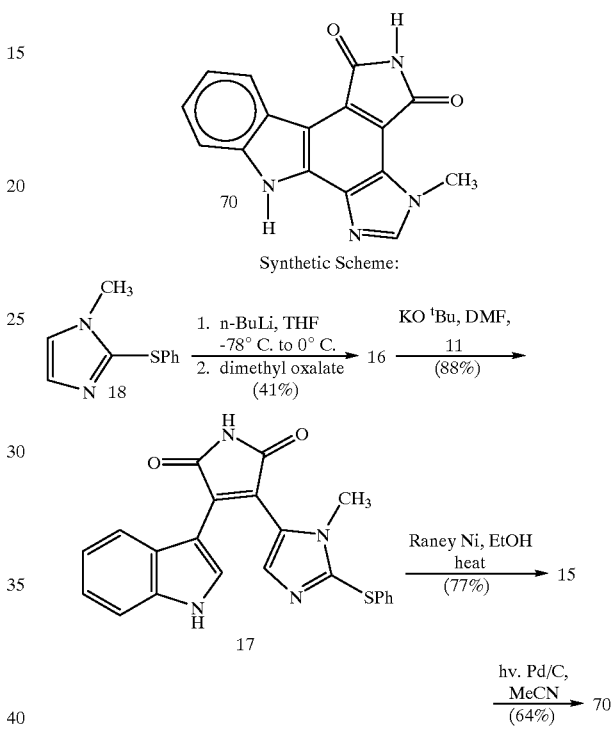

Methyl 2-(1-methyl-1H-2-phenylthioimidazol-5-yl) glyoxylate (16) To a cold (−78° C.), stirred solution of diisopropyl amine (0.175 mL, 1.25 mmol) in dry $Et_2O$ (2.0 mL) and dry DME (2.0 mL) was added a solution of n-BuLi (1.60 M in hexanes, 0.740 mL, 1.18 mmol) and the mixture was stirred for 0.5 h. A solution of 1-methyl-2-phenylthioimidazole# (18) (140 mg, 0.739 mmol) in dry $Et_2O$ (3.0 mL) was added and the solution was stirred at −78° C. for 0.25 h and at 0° C. for an additional 1 h. Dimethyl oxalate (520 mg, 4.40 mmol) was then added in one portion and the mixture was allowed to warm to rt and stir for an additional 3h. The reaction mixture was treated with saturated aqueous $NH_4Cl$ (5.0 mL) and EtOAc (20 ml). The phases were separated and the aqueous layer was extracted with EtOAc (2×20 mL). The combined organic extracts were washed with brine (10 mL), dried ($MgSO_4$), and concentrated. Flash chromatography (35 g of silica gel, 70:1 $CH_2Cl_2$—MeOH) of the crude material afforded 84.5 mg (41%) of 16 as a beige solid that exhibited mp 98–99° C.; IR (KBr) 1736, 1651, 1437, 1277, 1216, 1013 cm$^{-1}$; $^1$H NMR (CDCl$_3$, 400 MHz) 8.22 (s, 1H), 7.42–7.44 (m, 2H), 7.34–7.37 (m, 3H), 3.93 (s, 3H), 3.92 (s, 3H); $^{13}$C NMR (CDCl$_3$, 100 MHz) 172.9, 162.2, 151.8, 144.7, 132.4, 130.2, 129.9, 129.8, 129.1, 53.3, 34.3; HREIMS calcd for $C_{13}H_{12}N_2O_3S$ 276.0569, found 276.0569.

3-[4-(1-methyl-1H-2-phenylthio-imidazol-5-yl)-2,5-dioxo-2,5-dihydro-1-pyrrol-3-yl]-indole (17) To a stirred solution of t-BuOK (28 mg, 0.25 mmol) in DMF (1.0 mL) at rt was added sequentially 4A molecular seives (~50 mg) and a solution of 16 (28 mg, 0.10 mmol) and indole-3-acetamide 11 (22 mg, 0.13 mmol) in DMF (1.5 mL). The reaction mixture was heated to 40° C. and stirred for 48 h. The dark purple solution was treated with hydrochloric acid (1 N, 1.0 mL) and EtOAc (20 mL). The phases were separated and the aqueous layer was extracted with EtOAc (2×20 mL). The combined organic extracts were washed with brine (4×10 mL), dried ($MgSO_4$), and concentrated. Flash chromatography (20 g of silica gel, 30:1 $CH_2Cl_2$—MeOH) of the crude material afforded 35 mg (88%) of 17 as a red solid that exhibited; IR (KBr) 2500–3600, 1760, 1713, 1631, 1581, 1441, 1339, 744 $cm^{-1}$; $^1H$ NMR (400 MHz) 12.06 (bs, 1H), 11.19 (bs, 1H), 8.09 (d, 1 H, J=2.1 Hz), 7.46 (d, 1H, J=8.0 Hz), 7.14–7.31 (m, 6H), 7.03 (d, 1H, J=7.6 Hz), 6.81 (dd, 1H, J=8,8 Hz), 6.47 (d, 1H, J=8.1 Hz), 3.07 (s, 1H); $^{13}C$ NMR (100 MHz) 171.6, 171.4, 138.6, 136.4, 134.6, 133.7, 132.7, 131.8, 129.4, 127.4, 126.7, 126.6, 124.5, 120.8, 119.5, 117.9, 112.4, 104.8, 32.4; HREIMS calcd for $C_{22}H_{16}N_4O_2S$ 400.0994, found 400.0994.

Didemnimide C (15) To a refluxing solution of 17 (46.7 mg, 0.117 mmol) in EtOH (10 mL) was added Raney Ni (W-2, 50% slurry in water, ~120 mg) and the suspension was refluxed for 1 h. The reaction mixture was then cooled to rt and filtered through Celite. The Celite was washed with DMF (6 mL) and MeOH-TFA (100:1, 30 mL) and the combined organic washes were concentrated. The organic concentrate was then diluted with EtOAc (40 mL) and washed with $NaHCO_3$ (4×10 mL) brine (3×20 mL), dried ($MgSO_4$) and concentrated. Flash chromatography (25 g of silica gel, 10:1 $CH_2Cl_2$—MeOH) of the crude material afforded 26.4 mg (77%) of 15 as an orange solid that exhibited; IR (KBr) 3163, 3041, 1766, 1702, 1538, 1345, 1236, 1221, 748 $cm^{-1}$; $^1H$ NMR (400 MHz) 11.97 (bs, 1H), 11.09 (bs, 1H), 8.06 (d, 1H, J=2.6 Hz), 7.69 (bs, 1H), 7.44 (d, 1 H, J=8.1 Hz), 7.10 (dd, 1H, J=8,8 Hz), 6.78 (dd, 1H, J=8,8 Hz), 6.40 (d, 1H, J=8.1 Hz), 3.17 (s, 1H); $^{13}C$ NMR (100 MHz) 171.9, 171.7, 140.3, 136.4, 133.9, 132.0, 131.5, 124.7, 122.3, 120.5, 119.7, 112.2, 105.0, 32.0; HREIMS calcd for $C_{16}H_{12}N_4O_2$ 292.0960, found 292.0960

Cyclodidemnimide C (70) A solution of 15 (20.5 mg, 0.071 mmol) in MeCN (30.0 mL) was sparged with argon for 0.5 h. The orange mixture was then irradiated (450 Watt Hanovia medium pressure mercury vapour lamp, quartz reaction vessel) for 3.5 h. The reaction mixture was filtered through celite and washed with MeOH (30 mL) and DMF (40 mL) separately. The MeOH washings were concentrated under vacuo and tritrated with MeOH (3×10 mL) to afford 2.4 mg of 70 as a yellow residue. The DMF washings were concentrated to provide 10.1 (total of 12.5 mg, 64%) mg of 70 as a yellow solid which was only sparingly soluble in DMSO and exhibited; IR (KBr) 3257, 2951, 2726, 1734, 1703, 1505, 1479,1461,1393, 1326, 1225,1068,761, 744 $cm^{-1}$; $^1H$ NMR (400 MHz) 12.58 (bs, 1H), 11.04 (bs, 1H), 8.94 (d, 1H, J=7.7 Hz), 8.48 (s, 1H), 7.60 (d, 1H, J=8.1 Hz), 7.48 (dd, 1H, J=8,8 Hz), 7.30 (dd, 1H, J=8,8 Hz) 4.31 (s, 3H); $^{13}$NMR (100 MHz) 170.7, 169.1, 147.1, 140.6, 135.6, 133.8, 128.5, 126.2, 124.0, 123.6, 121.3, 120.1, 113.0, 111.6, 109.8, 35.1; HREIMS calcd for $C_{16}H_{10}N_4O_2$ 290.0804, found 290.0804.

In the G2 checkpoint inhibition assay, cyclodidemnimide C was found to have an $IC_{50}>100$ μM.

Example 7

Synthesis of Compounds Related to K252a, KT-6006, KT-6258

Synthesis of compounds of Formula III is achieved by the following synthetic schemes, outlined below and in Examples 8 and 9. The reaction conditions are those as provided in the cited references.

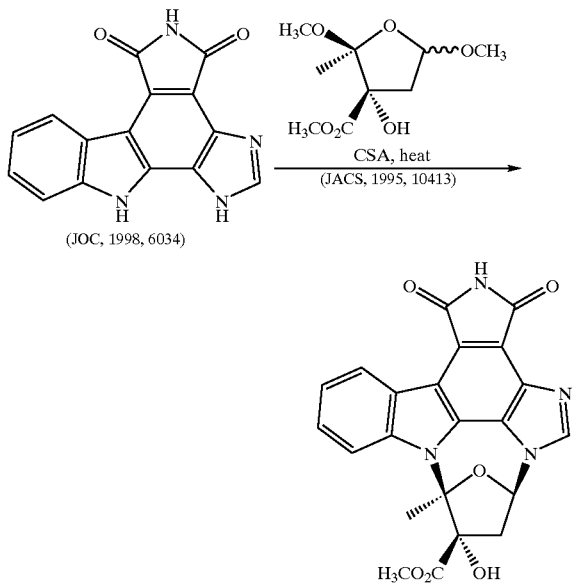

Example 8

Synthesis of Compounds Related to Arcyriarubin

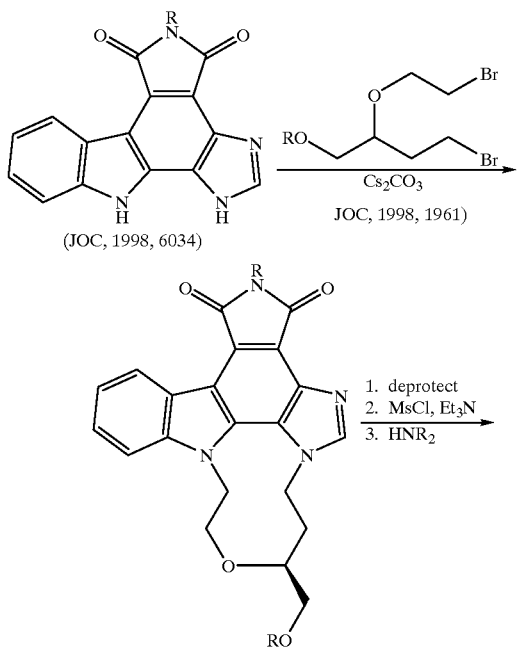

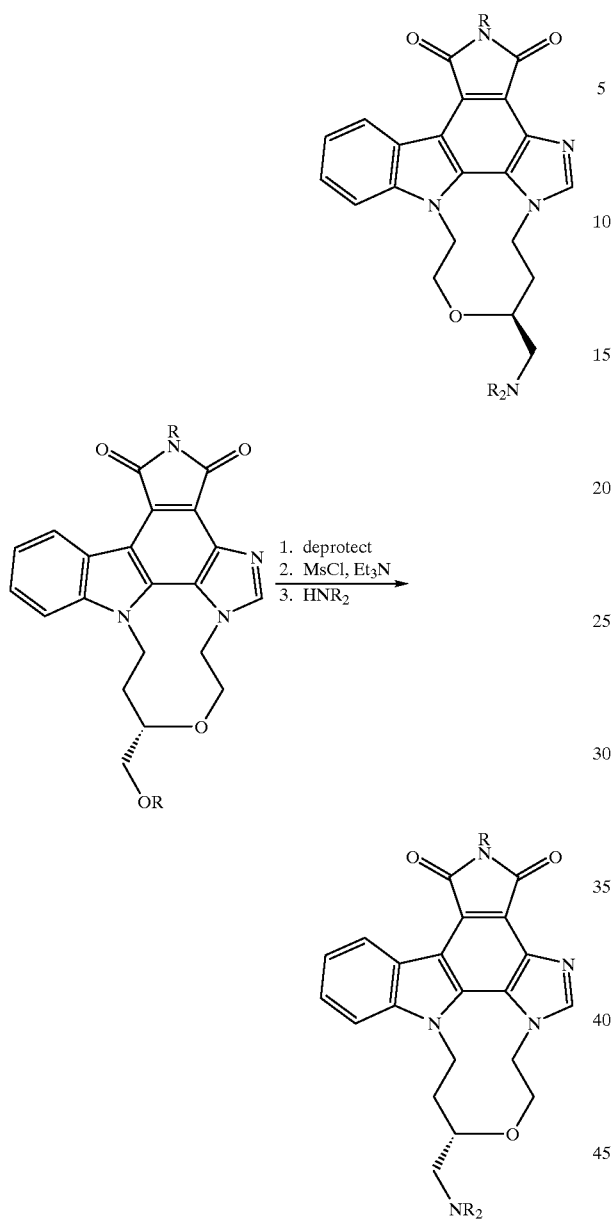
Also: References for Condensation
JOC 1998, 6053
TL, 1999, 1109
JOC, 1998, 6034

Example 9
Synthesis of Compounds Related to Staurosporine
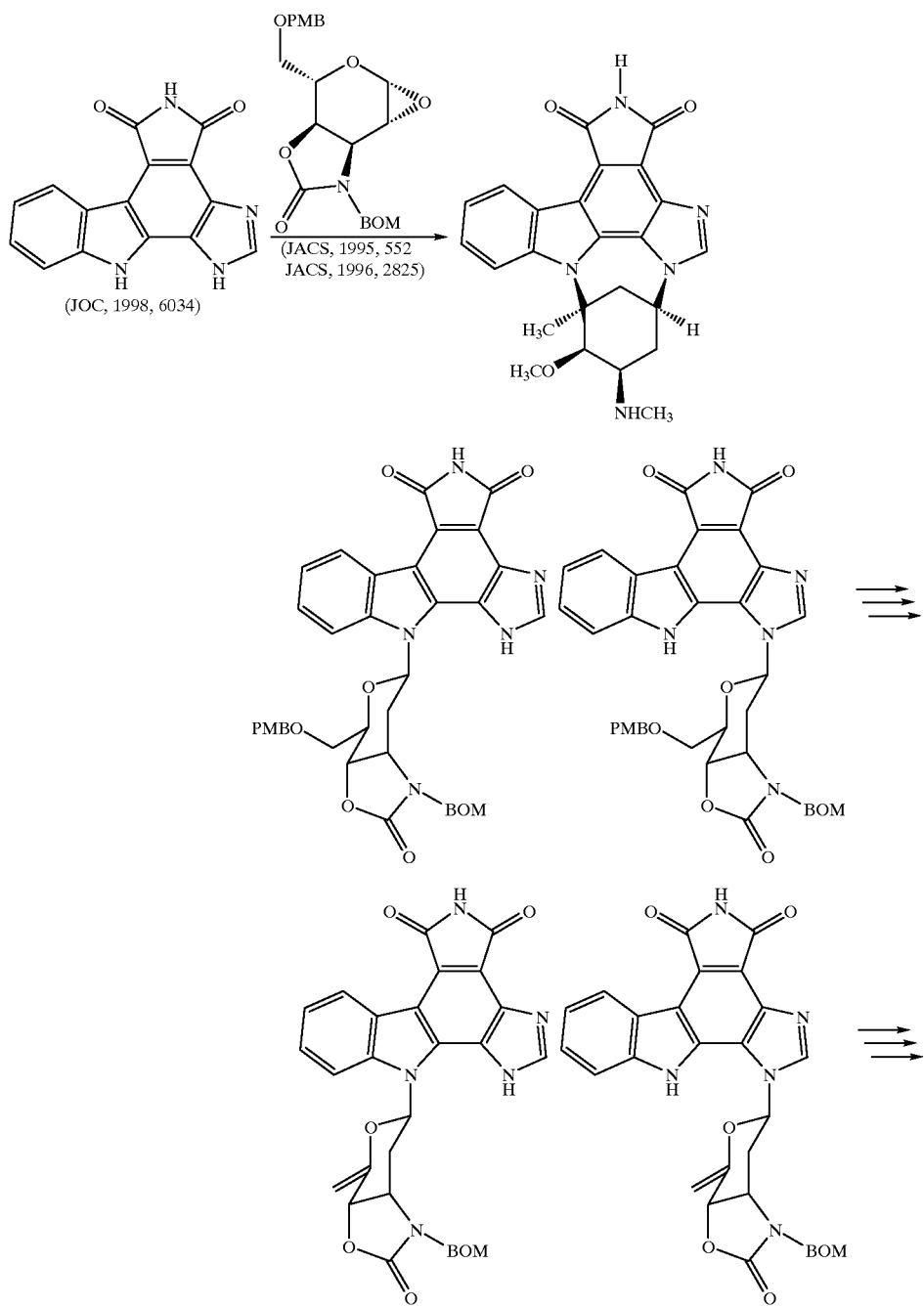

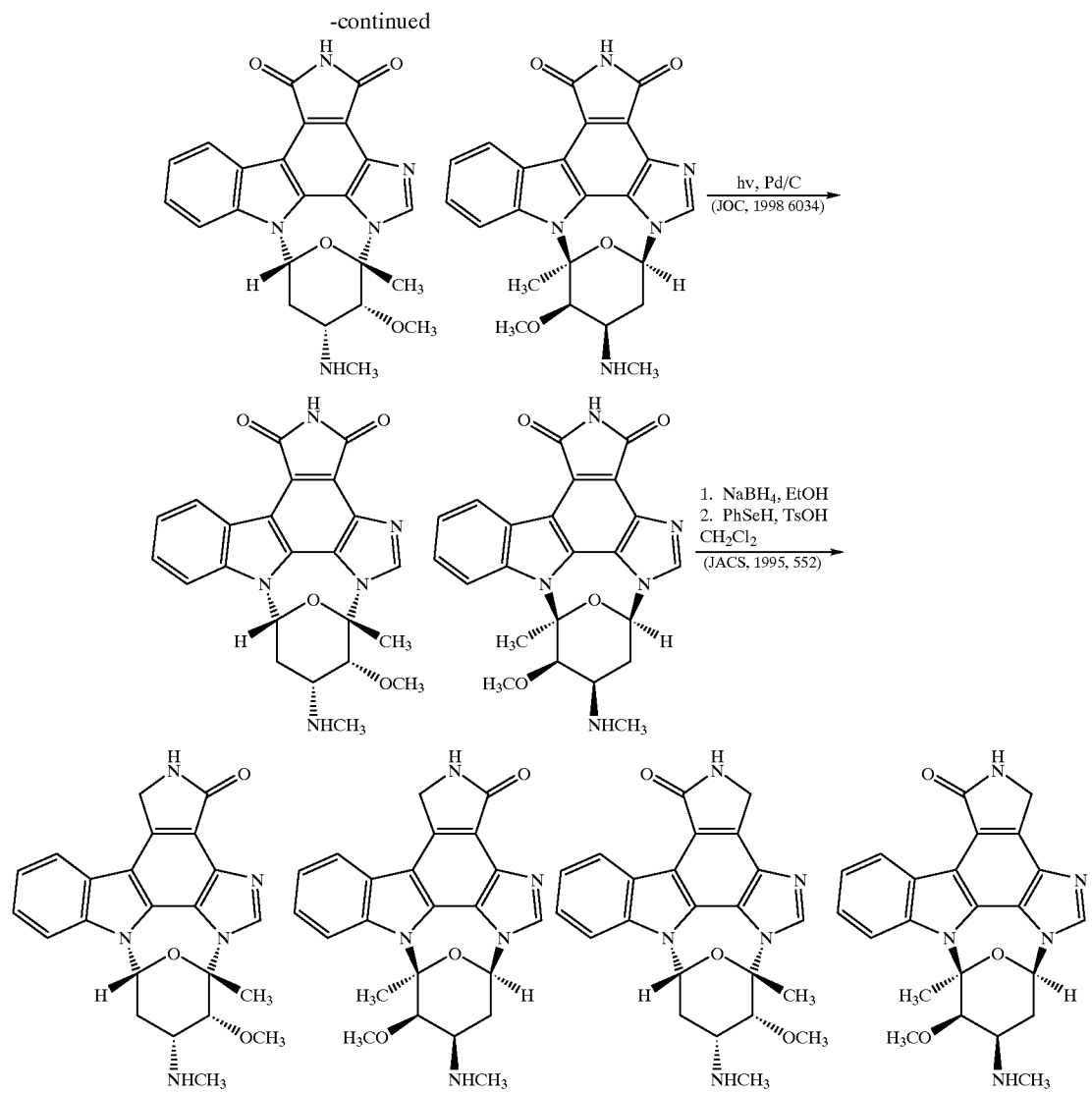
Example 10
Synthesis of Compounds Related to Rebeccamycin
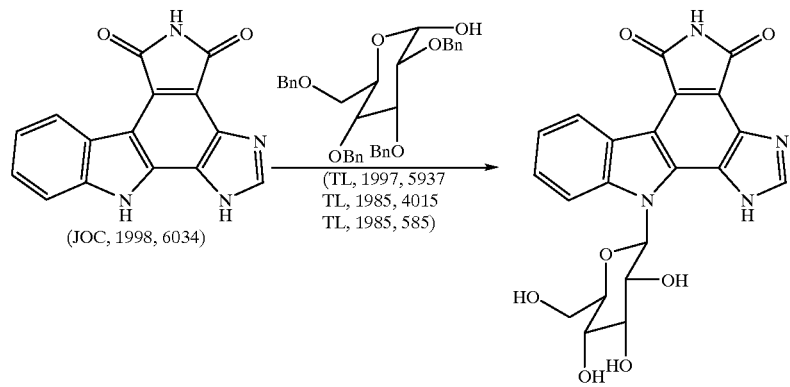

-continued

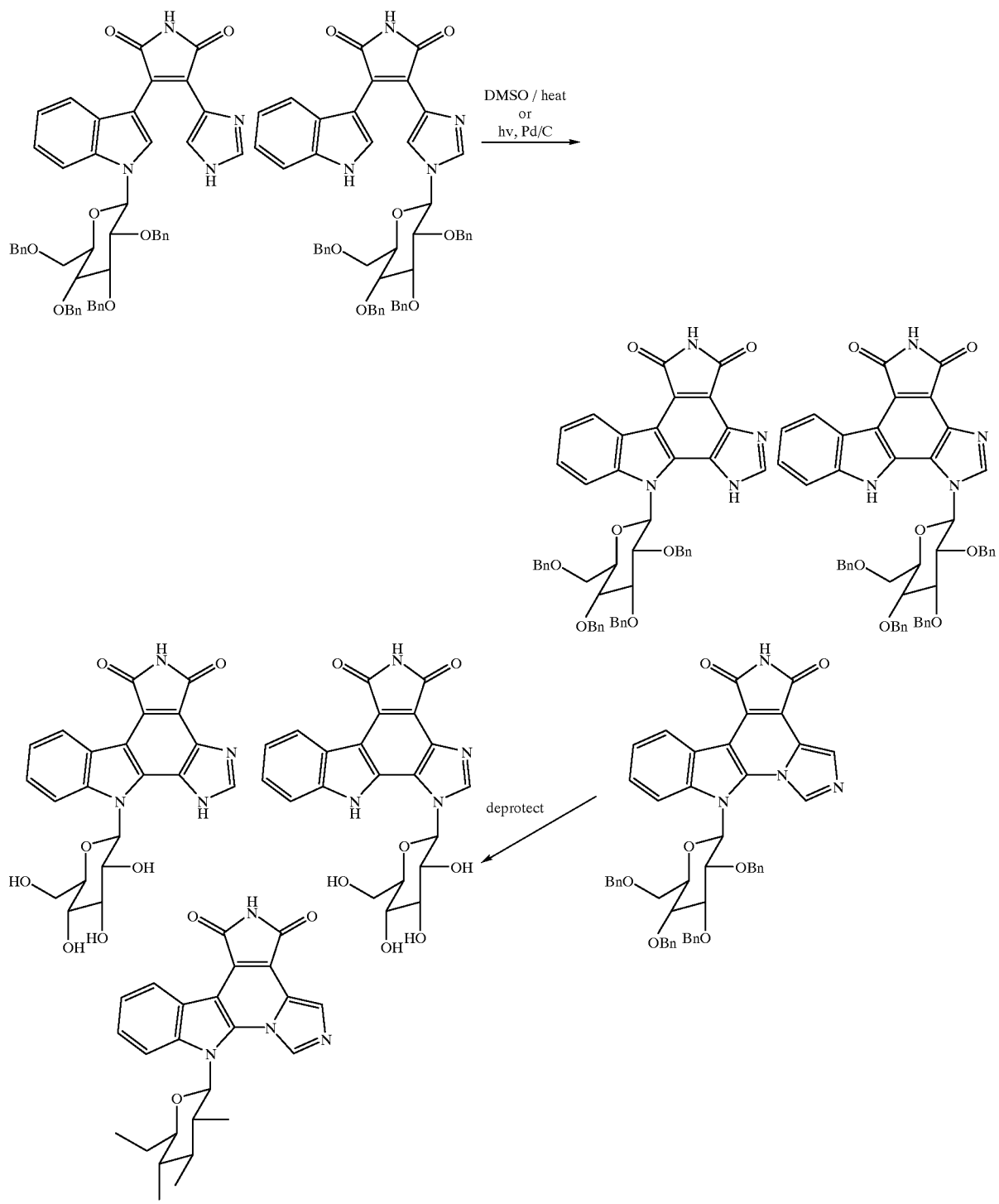

Example 11

Inhibition of Protein Kinases by Granulatimide Compounds

Granulatimide compounds and open forms of granulatimide compounds (RAB-004; RAB-006; RAB-011 and RAB-012) as shown in Table 2, were assayed for their inhibition of G2 checkpoint, as previously described, and for inhibition of protein kinase activity against a panel of protein kinases, including CDK1; GSK3b and IL1.

The GSK3b peptide substrate used was YRRAAVPPSPSLSRHSSPHQS (PO$_4$H$_2$)EDEE-amide. The ILK1 substrate is CKRRRLASLR-amide.

The test compounds were diluted to 250 μM in 1% DMSO, then serially diluted using three-fold dilution steps. 100% DMSO was used as a negative control.

Kinase reactions are performed at room temperature. The reaction mixture contains diluted test compound, the protein kinase, substrate and γ-$^{32}$P ATP. The mixture is incubated for 15 minutes, and the reaction mix spotted, and counted. The results are shown in Table 2.

TABLE 2

| Granulatimide Compound | | G2 checkpoint | CDK1 | GSK3b | ILK1 |
|---|---|---|---|---|---|
| Compound 4, ex. 4<br>RAB-009 | | >100 μM | >50 μM | 25 μM | >50 μM |
| Compound 5, ex. 4<br>RAB-010 | | 1 μM | 0.5 μM | 0.1 μM | 15 μM |
| iso-iso-granulatimide<br>RAB-007 | | 6 μM | 17 μM | 5 μM | >50 μM |
| Cyclodidemnimide C<br>RAB-005 | | inactive | >50 μM | >50 μM | >50 μM |
| Didemnimide C<br>RAB-006 | | inactive | 5 μM | 1 μM | 17 μM |

TABLE 2-continued

| Granulatimide Compound | | IC50 | | | |
|---|---|---|---|---|---|
| | | G2 checkpoint | CDK1 | GSK3b | ILK1 |
| Didemnimide A RAB-004 | | inactive | 10 μM | 0.6 μM | 0.6 μM |
| RAB-011 | | inactive | >50 μM | >50 μM | >50 μM |
| RAB-012 | | inactive | >50 μM | >50 μM | >50 μM |
| granulatimide | | 1.3 μM | 2 μM | 2 μM | >50 μM |
| isogranulatimide | | 1.8 μM | 10 μM | 0.5 μM | >50 μM |
| UCN-01 (control) | | n/d | 0.05 μM | 0.05 μM | >50 μM |
| staurosporine | | n/d | <1 nM | 1 nM | >50 μM |

These results demonstrate that granulatimide compounds can be active as kinase inhibitors, in addition to their activity inhibiting the G2 checkpoint. Interestingly, open granulatimides (didemnimide-like compounds), shown as RAB-004, RAB-006, RAB-011 and RAB-012, although inactive in the G2 checkpoint assay, can be active as kinase inhibitors.

Although various aspects of the present invention have been described in detail, it will be apparent that changes and modification of those aspects described herein will fall within the scope of the appended claims. All publications referred to herein are hereby incorporated by reference.

What is claimed is:

1. A compound having the structure:

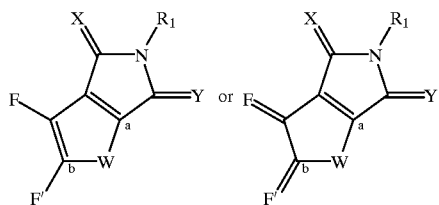

wherein:

in combination F and F' is $Ar_1$ as defined below;

$Ar_1$ is a monocyclic, bicyclic or tricyclic, fully or partially aromatic system containing five or six membered carbocyclic or, oxygen, nitrogen or sulphur containing heterocyclic rings, optionally substituted with R or Z;

W is selected from the group consisting of formula (i) and (ii), wherein the structures are as follows:

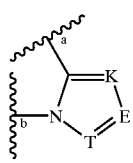

(i)

in which K, E and T are independently selected from the group consisting of: N, CR and CZ, and wherein R and Z are as defined below; and (ii)

in which K and E are independently selected from the group consisting of: N, CR and CZ, and wherein R, Z and Q are as defined below;

$R_1$, is selected from the group consisting of: R; RCO—; $Ar_2CO$—; and, $Ar_2CH_2$—, wherein $Ar_2$ is an aromatic substituent selected from the group consisting of: phenyl, naphthyl, anthracyl, phenanthryl, furan, pyrrole, thiophene, benzofuran, benzothiophene, quinoline, isoquinoline, imidazole, thiazole, oxazole, and pyridine, and $Ar_2$ may be optionally substituted with R or Z, wherein R and Z are as defined below;

R is selected from the group consisting of H; and a structural fragment having a saturated or unsaturated linear, branched, or cyclic, skeleton containing one to ten carbon atoms in which the carbon atoms may be optionally substituted with a substituent selected from the group consisting of: —OH; —$OR_3$; —$O_2CR_3$; —SH; —$SR_3$; —$SOCR_3$; —$NH_2$; —$NHR_3$; —$NH(R_3)_2$; —$NHCOR_3$; $NRCOR_3$; —I; —Br, —Cl; —F; —CN; —$CO_2H$; —$CO_2R_3$; —CHO; —$COR_3$; —$CONH_2$; —$CONHR_3$; —$CON(R_3)_2$; —COSH; —$COSR_3$; —$NO_2$; —$SO_3H$; —$SOR_3$; and —$SO_2R_3$, wherein $R_3$ is a linear, branched or cyclic, one to ten carbon saturated or unsaturated alkyl group;

Z is an optional substituent selected from the group consisting of: H; —OH; —OR; —$O_2CR$; —SH; —SR; —SOCR; —$NH_2$; —NHR; —$NH(R)_2$; —NHCOR; NRCOR; —I; —Br; —Cl; —F; —CN; —$CO_2H$; —$CO_2R$; —CHO; —COR; —$CONH_2$; —CONHR; —$CON(R)_2$; —COSH; —COSR; —$NO_2$; —$SO_3H$; —SOR; and, —$SO_2R$;

Q is selected from the group consisting of: $NR_1$; O; S, and $C(R)_2$; and

X and Y are independently selected from the group consisting of: O; H, OH; and $H_2$.

2. The compound of claim 1, wherein W is a five membered ring of formula (i) or (ii) comprising at least one nitrogen atom; and wherein E, K and T, where present are N or CH.

3. The compound of claim 2, wherein Q is NH.

4. The compound of claim 2, wherein $R_1$ is H or $CH_3$.

5. The compound of claim 1, wherein X and Y are oxygen.

6. The compound of claim 1, wherein F and F' are in combination represent the structure:

wherein each K is independently is selected from the group consisting of N, CR and CZ; and wherein Z and R are as defined in claim 1.

7. The compound of claim 6, wherein F and F' in combination have the bicyclic structure:

8. The compound of claim 7, wherein W is a five-membered ring formula (i) having one or two nitrogen atoms.

9. The compound of claim 8, having the structure:

10. A compound having the structure:

where $S_1$ is selected from the group consisting of wherein each K is independently selected from the group consisting of: N, CR and CZ, and wherein R and Z are as defined below;

$R_1$, is selected from the group consisting of: R; RCO—; $Ar_2CO$—; and, $Ar_2CH_2$—, wherein $Ar_2$ is an aromatic substituent selected from the group consisting of: phenyl, naphthyl, anthracyl, phenanthryl, furan, pyrrole, thiophene, benzofuran, benzothiophene, quinoline, isoquinoline, imidazole, thiazole, oxazole, and pyridine, and $Ar_2$ may be optionally substituted with R or Z;

R is selected from the group consisting of H; and a structural fragment having a saturated or unsaturated linear, branched, or cyclic, skeleton containing one to ten carbon atoms in which the carbon atoms may be optionally substituted with a substituent selected from the group consisting of: —OH; —OR$_3$; —O$_2$CR$_3$, —SH; —SR$_3$; —SOCR$_3$; —NH$_2$; —NHR$_3$; —NH(R$_3$)$_2$; —NHCOR$_3$; NRCOR$_3$; —I; —Br; —Cl; —F; —CN; —CO$_2$H; —CO$_2$R$_3$; —CHO; —COR$_3$; —CONH$_2$; —CONHR$_3$; —CON(R$_3$)$_2$; —COSH; —COSR$_3$; —NO$_2$; —SO$_3$H; —SOR$_3$; and —SO$_2$R$_3$, wherein R$_3$ is a linear, branched or cyclic, one to ten carbon saturated or unsaturated alkyl group;

Z is an optional substituent selected from the group consisting of: H; —OH; —OR; —O$_2$CR; —SH; —SR; —SOCR; —NH$_2$; —NHR; —NH(R)$_2$; —NHCOR; NRCOR; —I; —Br; —Cl; —F; —CN— —CO$_2$H; —CO$_2$R; —CHO; —COR; —CONH$_2$; —CONHR; —CON(R)$_2$; —COSH; —COSR; —NO$_2$; —SO$_3$H; —SOR; and, —SO$_2$R; and X and Y are independently selected from the group consisting of: O; H, OH; and H$_2$.

11. A compound having the formula:

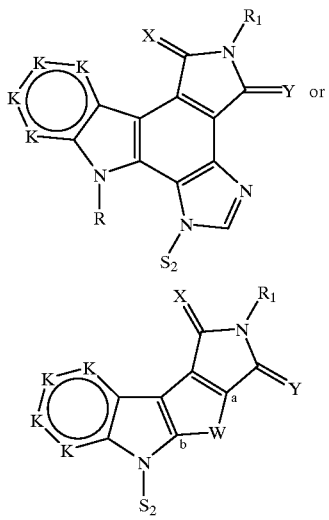

wherein each K is independently selected from the group consisting of: N, CR and CZ, and wherein R and Z are as defined below; and where W has the formula (ii)

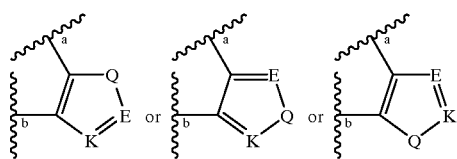

(ii)

in which K and E are independently selected from the group consisting of: N, CR and CZ, and wherein R, Z and Q are as defined below;

R$_1$, is selected from the group consisting of: R; RCO—; Ar$_2$CO—; and, Ar$_2$CH2—, wherein Ar$_2$ is an aromatic substituent selected from the group consisting of: phenyl, naphthyl, anthracyl, phenanthryl, furan, pyrrole, thiophene, benzofuran, benzothiophene, quinoline, isoquinoline, imidazole, thiazole, oxazole, and pyridine, and Ar$_2$ may be optionally substituted with R or Z, wherein R and Z are as defined below;

R is selected from the group consisting of H; and a structural fragment having a saturated or unsaturated linear, branched, or cyclic, skeleton containing one to ten carbon atoms in which the carbon atoms may be optionally substituted with a substituent selected from the group consisting of: —OH; —OR$_3$; —O$_2$CR$_3$, —SH; —SR$_3$; —SOCR$_3$; —NH$_2$; —NHR$_3$; —NH(R$_3$)$_2$; —NHCOR$_3$; NRCOR$_3$; —I; —Br; —Cl; —F; —CN; —CO$_2$H; —CO$_2$R$_3$; —CHO; —COR$_3$; —CONH$_2$; —CONHR$_3$; —CON(R$_3$)$_2$; —COSH; —COSR$_3$; —NO$_2$; —SO$_3$H; —SOR$_3$; and —SO$_2$R$_3$, wherein R$_3$ is a linear, branched or cyclic, one to ten carbon saturated or unsaturated alkyl group;

Z is an optional substituent selected from the group consisting of: H; —OH; —OR; —O$_2$CR; —SH; —SR; —SOCR; —NH$_2$; —NHR; —NH(R)$_2$; —NHCOR; NRCOR; —I; —Br; —Cl; —F; —CN; —CO$_2$H; —CO$_2$R; —CHO; —COR; —CONH$_2$; —CONHR; —CON(R)$_2$; —COSH; —COSR; —NO$_2$; —SO$_3$H; —SOR; and, —SO$_2$R;

Q is selected from the group consisting of: NR$_1$; O; S, and C(R)$_2$; and

X and Y are independently selected from the group consisting of: O; H, OH; and H$_2$;

S$_2$ has the formula (iv)

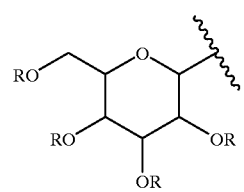

(iv)

or S$_2$ is a linear alkyl chain of from one to eight carbon atoms containing a terminal NR$_2$, where R$_2$ is an alkyl group of from 1 to 6 carbon atoms, branched, linear or cyclic.

12. A compound having the formula:

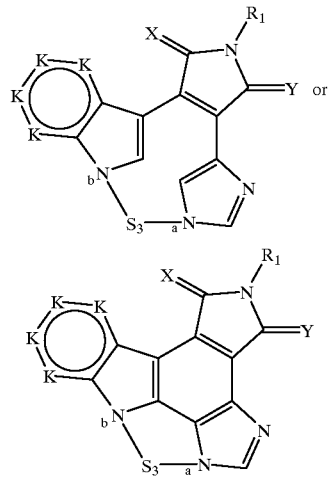

wherein each K is independently selected from the group consisting of: N, CR and CZ, and wherein R and Z are as defined below;

R$_1$, is selected from the group consisting of: R; RCO—; Ar$_2$CO—; and, Ar$_2$CH$_2$—, wherein Ar$_2$ is an aromatic substituent selected from the group consisting of: phenyl, naphthyl, anthracyl, phenanthryl, furan, pyrrole, thiophene, benzofuran, benzothiophene, quinoline, isoquinoline, imidazole, thiazole, oxazole, and pyridine, and Ar$_2$ may be optionally substituted with R or Z;

R is selected from the group consisting of H; and a structural fragment having a saturated or unsaturated linear, branched, or cyclic, skeleton containing one to ten carbon atoms in which the carbon atoms may be optionally substituted with a substituent selected from the group consisting of: —OH; —OR$_3$; —O$_2$CR$_3$, —SH; —SR$_3$; —SOCR$_3$; —NH$_2$; —NHR$_3$; —NH(R$_3$)$_2$; —NHCOR$_3$; NRCOR$_3$; —I; —Br; —Cl; —F; —CN; —CO$_2$H; —CO$_2$R$_3$; —CHO; —COR$_3$; —CONH$_2$; —CONHR$_3$; —CON(R$_3$)$_2$; —COSH; —COSR$_3$; —NO$_2$; —SO$_3$H; —SOR$_3$; and —SO$_2$R$_3$, wherein R$_3$ is a linear, branched or cyclic, one to ten carbon saturated or unsaturated alkyl group;

Z is an optional substituent selected from the group consisting of: H; —OH; —OR; —O$_2$CR; —SH; —SR; —SOCR; —NH$_2$; —NHR; —NH(R)$_2$; —NHCOR; NRCOR; —I; —Br; —Cl; —F; —CN; —CO$_2$H; —CO$_2$R; —CHO; —COR; —CONH$_2$; —CONHR; —CON(R)$_2$; —COSH; —COSR; —NO$_2$; —SO$_3$H; —SOR; and, —SO$_2$R;

X and Y are independently selected from the group consisting of: O; H, OH; and H$_2$;

S$_3$ is

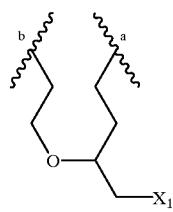

and X$_1$ is selected from the group of N(CH$_3$)$_2$, NHCH$_3$, NH$_2$,

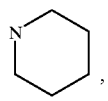

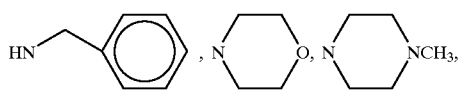

or S$_3$ is a linear bridge of between five and eight carbon, nitrogen or oxygen atoms, where the bridge carbon atoms may have OR or NR$_2$ substituents and the bridge nitrogen atoms may have R substituents, where R is a defined above.

13. A compound having the structure:

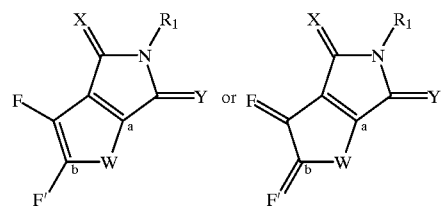

wherein:

R$_1$ is H or CH$_3$;

in combination F and F' have the structure:

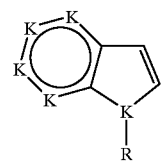

wherein each K is independently is selected from the group consisting of N, CR and CZ and wherein R and Z are as defined below;

W is a five-membered ring of formula (i) and (ii) comprising at least one nitrogen atom; wherein the structures are as follows:

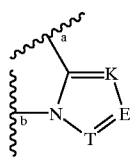
(i)

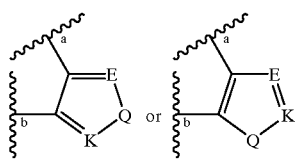
(ii)

in which K and E are independently selected from the group consisting of: N, CR and CZ, and Q is selected from the group consisting of: NR; O; S, and C(R)$_2$;

and wherein R is selected from the group consisting of H; and a structural fragment having a saturated or unsaturated linear, branched, or cyclic, skeleton containing one to ten carbon atoms in which the carbon atoms may be optionally substituted with a substituent selected from the group consisting of: —OH; —OR$_3$; —O$_2$CR$_3$, —SH; —SR$_3$; —SOCR$_3$; —NH$_2$; —NHR$_3$; —NH(R$_3$)$_2$; —NHCOR$_3$; NRCOR$_3$; —I; —Br; —Cl; —F; —CN; —CO$_2$H; —CO$_2$R$_3$; —CHO; —COR$_3$; —CONH$_2$; —CONHR$_3$; —CON(R$_3$)$_2$; —COSH; —COSR$_3$; —NO$_2$; —SO$_3$H; —SOR$_3$; and —SO$_2$R$_3$, wherein R$_3$ is a linear, branched or cyclic, one to ten carbon saturated or unsaturated alkyl group;

Z is an optional substituent selected from the group consisting of: H; —OH; —OR; —O$_2$CR; —SH; —SR;

—SOCR; —NH$_2$; —NHR; —NH(R)$_2$; —NHCOR; NRCOR; —i; —Br; —Cl; —F; —CN; —CO$_2$H; —CO$_2$R; —CHO; —COR; —CONH$_2$; —CONHR; —CON(R)$_2$; —COSH; —COSR; —NO$_2$; —SO$_3$H; —SOR; and, —SO$_2$R; and X and Y are independently selected from the group consisting of: O; H, OH; and H$_2$.

14. A pharmaceutical formulation comprising a pharmaceutically acceptable carrier and a compound having the structure:

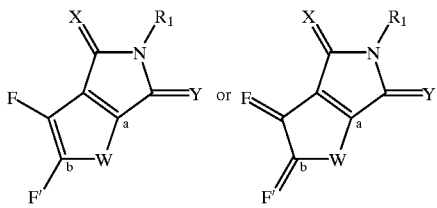

wherein:
in combination F and F' is Ar$_1$ as defined below;
Ar$_1$ is a monocyclic, bicyclic or tricyclic, fully or partially aromatic system containing five or six membered carbocyclic or, oxygen, nitrogen or sulphur containing heterocyclic rings, optionally substituted with R or Z;
W is selected from the group consisting of formula (i); (ii) or (iii), wherein the structures are as follows:

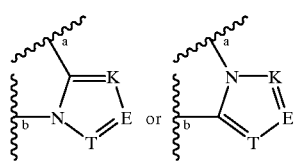

(i)

in which K, E and T are independently selected from the group consisting of: N, CR and CZ, and wherein R and Z are as defined below;

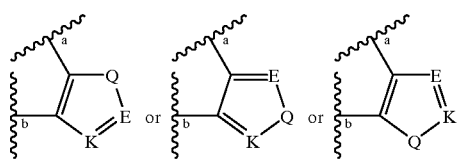

(ii)

in which K and E are independently selected from the group consisting of: N, CR and CZ, and wherein R, Z and Q are as defined below; and
R$_1$, is selected from the group consisting of: R; RCO—; Ar$_2$CO—; and, Ar$_2$CH$_2$—, wherein Ar$_2$ is an aromatic substituent selected from the group consisting of: phenyl, naphthyl, anthracyl, phenanthryl, furan, pyrrole, thiophene, benzofuran, benzothiophene, quinoline, isoquinoline, imidazole, thiazole, oxazole, and pyridine, and Ar$_2$ may be optionally substituted with R or Z, wherein R and Z are as defined below;

R is selected from the group consisting of H; and a structural fragment having a saturated or unsaturated linear, branched, or cyclic, skeleton containing one to ten carbon atoms in which the carbon atoms may be optionally substituted with a substituent selected from the group consisting of: —OH; —OR$_3$; —O$_2$CR$_3$, —SH; —SR$_3$; —SOCR$_3$; —NH$_2$; —NHR$_3$; —NH(R$_3$)$_2$; —NHCOR$_3$; NRCOR$_3$; —I; —Br; —Cl; —F; —CN; —CO$_2$H; —CO$_2$R$_3$; —CHO; —COR$_3$; —CONH$_2$; —CONHR$_3$; —CON(R$_3$)$_2$; —COSH; —COSR$_3$; —NO$_2$; —SO$_3$H; —SOR$_3$; and —SO$_2$R$_3$, wherein R$_3$ is a linear, branched or cyclic, one to ten carbon saturated or unsaturated alkyl group;

Z is an optional substituent selected from the group consisting of: H; —OH; —OR; —O$_2$CR; —SH; —SR; —SOCR; —NH$_2$; —NHR; —NH(R)$_2$; —NHCOR; NRCOR; —I; —Br; —Cl; —F; —CN—CO$_2$H; —CO$_2$R; —CHO; —COR; —CONH$_2$; —CONHR; —CON(R)$_2$; —COSH; —COSR; —NO$_2$; —SO$_3$H; —SOR; and, —SO$_2$R;

Q is selected from the group consisting of: NR$_1$; O; S, and C(R)$_2$; and

X and Y are independently selected from the group consisting of: O; H, OH; and H$_2$.

15. A method of inhibiting the G2 checkpoint in a cell, the method comprising:
administering to a cell a compound according to claim 1, in a dose effective to inhibit said G2 checkpoint.

16. A method of enhanced killing of a hyperproliferative cell, the method comprising:
administering to a cell a compound according to claim 1, in a dose effective to inhibit the G2 checkpoint.

17. The method of claim 16, wherein said hyperproliferative cell is p53 negative.

18. The method of claim 17, further comprises administration of a cytotoxic therapy.

19. The method according to claim 18, wherein said cytotoxic therapy is radiation treatment.

20. The method of claim 18, wherein said cytotoxic therapy is administration of a DNA-damaging chemotherapeutic agent.

21. A method of inhibiting a protein kinase, the method comprising:
contacting said protein kinase with a dose of a compound of claim 1, in an amount effective to inhibit said protein kinase.

22. A method of treating a condition characterized by a defect in protein kinase mediated signaling, the method comprising:
administering a dose of a compound of claim 1, in an amount effective to inhibit said protein kinase.

* * * * *